US00RE37438B1

(19) United States
(12) Reissued Patent
Oplinger et al.

(10) Patent Number: US RE37,438 E
(45) Date of Reissued Patent: Nov. 6, 2001

(54) ACETAMIDINE DERIVATIVES AND THEIR USE AS INHIBITORS FOR THE NITRIC OXIDE SYNTHASE

(75) Inventors: Jeffrey Alan Oplinger, Cary; Edward Patrick Garvey, Chapel Hill; Eric Steven Furfine, Durham; Barry George Shearer, Cary; Jon Loren Collins, Durham, all of NC (US)

(73) Assignee: Glaxo Wellcome Inc., Research Triangle Park, NC (US)

(21) Appl. No.: 09/304,947

(22) PCT Filed: Dec. 20, 1995

(86) PCT No.: PCT/GB95/02978

§ 371 Date: Jun. 17, 1997

§ 102(e) Date: Jun. 17, 1997

(87) PCT Pub. No.: WO96/19440

PCT Pub. Date: Jun. 27, 1996

Related U.S. Patent Documents

Reissue of:
(64) Patent No.: 5,866,612
Issued: Feb. 2, 1999
Appl. No.: 08/860,154
Filed: Jun. 17, 1997

(30) Foreign Application Priority Data

Dec. 20, 1994 (GB) ..... 9425701

(51) Int. Cl.[7] ..... A61K 31/155; C07C 257/14

(52) U.S. Cl. ..... 514/637; 514/520; 514/538; 514/631; 558/418; 560/27; 560/35; 564/225; 564/243; 564/244; 564/245; 564/246

(58) Field of Search ..... 514/520, 564, 514/538, 631, 637; 558/418; 560/27, 35; 562/405, 440; 564/225, 243, 244, 245, 246

(56) References Cited

FOREIGN PATENT DOCUMENTS

| | | |
|---|---|---|
| 2020155 | 11/1971 | (DE) . |
| 2300221 | 7/1974 | (DE) . |
| 2601137 | 7/1976 | (DE) . |
| 2557651 | 6/1977 | (DE) . |
| 1183135 | 3/1970 | (GB) . |
| WO9313055 | 7/1993 | (WO) . |

OTHER PUBLICATIONS

J. Oszczapowicz, et al, *Chemical Abstracts,* vol. 102, No. 10, Mar. 11, 1985 Columbus, Ohio, US; Et *J. Chromatogr.,* vol. 315 (1984) pp. 95–100.

Saari, W.S., et al, Trichloroacetamidines, a new class of positive inotropic agents, *Journal of Medicinal Chemistry,* vol. 21, No. 12 (1978) Washington U.S., pp. 1283–1290.

T. T. Conway, et al., *Chemical Abstracts,* vol. 68, no. 21, May 20, 1968, Columbus, Ohio US; Et *J. Pharm. Sci.,* vol. 57, No. 3 (1968) pp. 455–459.

Parulkar, A. P., et al., N–Heteroaralkyl substituted . alpha.–a-midinium thiolsulfates, *Journal of Heterocyclic Chemistry,* vol. 3, No. 4 (1996) Provo US, pp. 472–475.

Bolhoffer, W. A., et al. 2–Mercaptoacetamidines as gastric antisecretory agents, *Journal of Medicinal Chemistry* vol. 22, No. 3 (1979) Washington US, pp. 295–301.

Keir, W. F., et al. Amidinoacetamides in the synthesis of pyrimidines, imidazoles and purines, *Journal of the Chemical Society,* Perkin Transactions 1 (1976) Letchworth GB, pp. 1847–1852.

*Database Crossfire,* Beilstein Informationssysteme GmbH, Frankfurt DE, see BRN 2346409 Et Chem. Ber., vol. 93 (1960) pp. 2230–2238.

*Database Crossfire,* Beilstein Informationssysteme GmbH, Frankfurt DE, see BRN 3777937 Et Justus Liebigs Ann. Chem., vol. 575 (1952) p. 90ff.

(List continued on next page.)

*Primary Examiner*—Shailendra Kumar
(74) *Attorney, Agent, or Firm*—Lorie Ann Morgan

(57) ABSTRACT

A class of acetamidine derivatives of general formula (I)

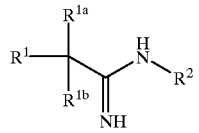

wherein $R^1$ is hydrogen, $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl, provided that $R^3$ is not $NR^5R^6$ when X is oxygen or $S(O)_n$; $R^{1a}$ and $R^{1b}$ are independently selected from hydrogen and halo; $R^2$ is a $C_{1-14}$ hydrocarbyl group which may optionally contain one or two heteroatoms, the group $R^2$ being optionally substituted by one or more groups independently selected from halo; $N_3$; nitro; $CF_3$; $ZR^7$ wherein Z is oxygen, $C(O)_{m'}$ wherein m' is 1 or 2, $S(O)_{n'}$ wherein n' is 0, 1 or 2, or a group $NR^8$ wherein $R^8$ is hydrogen or $C_{1-6}$ alkyl and $R^7$ is hydrogen, $C_{1-6}$ alkyl or a group $NR^9R^{10}$ wherein $R^9$ and $R^{10}$ are independently hydrogen or $C_{1-6}$ alkyl; or $R^2$is substituted by a group (a)

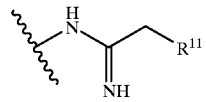

wherein $R^{11}$ has a definition the same as for $R^1$;
with the proviso that when $R^1$ is a $C_{1-6}$ alkyl group and $R^2$ is a $C_{1-14}$ hydrocarbyl substituted by two groups $ZR^7$ wherein one group $ZR^7$ is $CO_2H$, the other group $ZR^7$ is not $NH_2$;
and salts thereof, methods for the manufacture thereof, and therapies, particularly inhibtion of nitric oxide synthase, is disclosed.

16 Claims, No Drawings

OTHER PUBLICATIONS

*Database Crossfire,* Beilstein Informationssysteme GmbH, Frankfurt, DE, see BRN 7088281, see BRN 7089080 Et Farmaco Ed. Sci., vol. 43, No. 1 (1988) pp. 102–112.

*Database Crossfire,* Beilstein Informationssysteme GmbH, Frankfurt, DE, see BRN 1790943 Et J. Chem. Soc. (1947) p. 730.

*Database Crossfire,* Beilstein Informationssysteme GmbH, Frankfurt DE, see BRN 394415 Et Can. J. Chem., vol. 39 (1961) pp. 761–764.

*Database Crossfire,* Beilstein Informationssysteme GmbH, Frankfurt DE, see BRN 3278146 Et Recl. Trav. Chim. Pays–Bas, vol. 70 (1951) p. 638, 641.

*Database Crossfire,* Beilstein Informationssysteme GmbH, Frankfurt DE, see BRN 2717900 Et GB ,A, 861 526 (1958).

*Database Crossfire,* Beilstein Informationssysteme GmbH, Frankfurt DE, see BRN 746863 Et Bull Chem Soc. Jpn, vol. 45 (1972) pp. 2010–2015.

*Database Crossfire,* Beilstein Informationssysteme GmbH, Frankfurt DE, see BRN 473624 Et J. Indian Chem. Soc., vol. 39 (1962) pp. 208–210.

*Database Crossfire,* Beilstein Informationssysteme GmbH, Frankfurt DE, see BRN 113878 Et J. Heterocycl. Chem., vol. 12 (1975) p. 407.

*Database Crossfire,* Beilstein Informationssysteme GmbH, Frankfurt DE, see BRN 6423899 Et Gazz. Chim. Ital., vol. 113, No. 1–2 (1983) pp. 77–82.

*Journal of Medicinal Chemistry,* vol. 37, No. 23, Nov. (1994) Washington US, pp. 3886–3888.

ACETAMIDINE DERIVATIVES AND THEIR USE AS INHIBITORS FOR THE NITRIC OXIDE SYNTHASE

Matter enclosed in heavy brackets [ ] appears in the original patent but forms no part of this reissue specification; matter printed in italics indicates the additions made by reissue.

This application is filed pursuant to 35 USC section 371 as a United States National Phase Application of International Application No. PCT/GB95/02978 filed Dec. 20, 1995 which claims priority from GB9425701.1 filed Dec. 20, 1994.

The present invention relates to acetamidine derivatives, to methods for their manufacture, to pharmaceutical compositions containing them and to their use in therapy, in particular their use as selective inhibitors of nitric oxide synthase.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrite and other nitrovasodilators. The recent identification of EDRF as NO has coincided with the discovery of a biochemical pathway by which NO is synthesised from the amino acid L-arginine by the enzyme NO synthase.

NO is the endogenous stimulator of the soluble guanylate cyclase enzyme and is involved in a number of biological actions in addition to endothelium-dependent relaxation including cytotoxicity of phagocytic cells and cell-to-cell communication in the central nervous system (see Moncada et al, Biochemical Pharmacology, 38, 1709–1715 (1989) and Moncada et al, Pharmacological Reviews, 43, 109–142 (1991)). It is now thought that excess NO production may be involved in a number of conditions, particularly conditions which involve systemic hypotension such as septic (toxic) shock and therapy with certain cytokines.

The synthesis of NO from L-arginine can be inhibited by the L-arginine analogue, NG-monomethyl-L-arginine (L-NMMA), and the therapeutic use of L-NMMA for the treatment of septic (toxic) shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three isoenzymes of NO synthase (reviewed in Knowles and Moncada, Biochem. J. (1994) 298, 249–258) as follows:

(i) a constitutive, Ca++/calmodulin dependent enzyme (eNOS) which is present in vascular endothelial cells, and that releases NO in response to receptor or physical stimulation.

(ii) a constitutive, Ca++/calmodulin dependent enzyme (nNOS), located in the brain and some peripheral nervous systems, that releases NO in response to receptor or physical stimulation.

(iii) a Ca++ independent enzyme (INOS) which is induced after activation of vascular smooth muscle, macrophages, endothelial cells, and a number of other cells by endotoxin and cytokines. Once expressed, this inducible NO synthase synthesises NO for long periods.

The NO released by eNOS and nNOS acts as a transduction mechanism underlying several physiological responses. The NO produced by iNOS acts as a cytotoxic molecule for tumour cells and invading micro-organisms. It also appears that the adverse effects of excess NO production, in particular pathological vasodilatation and tissue damage, may result largely from the effects of NO synthesised by iNOS.

The NO synthase inhibitors proposed for therapeutic use so far, such as L-NMMA and nitroarginine, are non-selective in that they inhibit all the NO synthase isoenzymes. Use of such a non-selective NO synthase inhibitor requires that great care is taken in order to avoid the potentially serious consequences of over-inhibition of the eNOS including hypertension and possible thrombosis and tissue damage. In particular, in the case of the therapeutic use of L-NMMA for the treatment of septic and/or toxic shock it has been recommended that the patient must be subject to continuous blood pressure monitoring throughout the treatment. Thus, whilst non-selective NO synthase inhibitors have therapeutic utility provided that appropriate precautions are taken, NO synthase inhibitors which are selective in the sense that they inhibit iNOS or nNOS to a considerably greater extent than eNOS would be of even greater therapeutic benefit and much easier to use.

We have found that a class of acetamidine derivatives are inhibitors of NO synthase, and are useful in the treatment of systemic hypotension, and in particular the treatment of septic shock. In addition these compounds show a marked selectivity of one of the isoenzyme with little or no inhibition of the other isoenzymes.

Accordingly, the present invention provides an acetamidine derivative of formula (I)

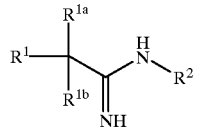

or a salt thereof, wherein $R^1$ is hydrogen, a $C_{1-6}$ hydrocarbyl group optionally substituted by halo, halo, nitro, cyano or a group $XR^3$ wherein X is oxygen $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl, provided that $R^3$ is not $NR^5R^6$ when X is oxygen or $S(O)_n$;

$R^{1a}$ and $R^{1b}$ are independently selected from hydrogen or halo;

$R^2$ is a $C_{1-14}$ hydrocarbyl group which may optionally contain one or two heteroatoms, the group $R^2$ being optionally substituted by one or more groups independently selected from halo; $N_3$; nitro; $CF_3$; $ZR^7$ wherein Z is oxygen, $C(O)_{m'}$ wherein m' is 1 or 2, $S(O)_{n'}$ wherein n' is 0, 1 or 2, or a group $NR^8$ wherein $R^8$ is hydrogen or $C_{1-6}$ alkyl and $R^7$ is hydrogen, $C_{1-6}$ alkyl or a group $NR^9R^8$ wherein $R^9$ and $R^{10}$ are independently hydrogen or $C_{1-6}$ alkyl; or $R^2$ is substituted by a group

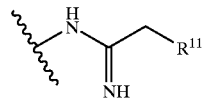

wherein $R^{11}$ has a definition the same as for $R^1$;

with the proviso that when $R^1$ is a $C_{1-6}$ alkyl group and $R^2$ is a $C_{1-14}$ hydrocarbyl substituted by two groups $ZR^7$ wherein one group $ZR^7$ is $CO_2H$, the other groups $ZR^7$ is not $NH_2$.

In preferred embodiments, $R^1$ is hydrogen, a $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^3$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl, provided that $R^3$ is not $NR^5R^6$ when X is oxygen or $S(O)_n$; and/or $R^{1a}$ and $R^{1b}$ are independently selected from hydrogen or halo; and/or $R^2$ is a $C_{1-14}$ hydrocarbyl group which may optionally contain one or two heteroatoms, the group $R^2$ being optionally substituted by one or two groups which may be the same or different, and are selected from halo; $ZR^7$ wherein Z is oxygen, $C(O)_{m'}$ wherein m' is 1 or 2, $S(O)_{n'}$ wherein n' is 0, 1 or 2, or a group $NR^8$ wherein $R^8$ is hydrogen or $C_{1-6}$ alkyl and $R^7$ is hydrogen, $C_{1-6}$ alkyl or a group $NR^9R^{10}$ wherein $R^9$ and $R^{10}$ are independently hydrogen or $C_{1-6}$ alkyl; or $R^2$ is substituted by a group

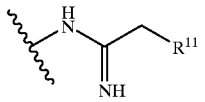

wherein $R^{11}$ has a definition the same as for $R^1$;

with the proviso that when $R^1$ is a $C_{1-6}$ alkyl group and $R^2$ is a $C_{1-14}$ hydrocarbyl substituted by two groups $ZR^7$ wherein one group $ZR^7$ is $CO_2H$, the other group $ZR^7$ is not $NH_2$.

Suitably, $R^1$ is hydrogen, $C_{1-4}$ alkyl, halo, nitro, $NR^4R^3$ or $SR^3$ wherein $R^3$ and $R^4$ is as hereinbefore defined.

Suitably, $R^2$ is a $C_{1-8}$ hydrocarbyl group optionally containing one or two heteroatoms, each group $R^2$ being optionally substituted by one group $ZR^7$ wherein Z and $R^7$ are as hereinbefore defined, or a group

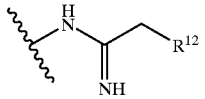

wherein $R^{12}$ is fluoro, hydrogen or $NH_2$.

Preferably $R^1$ is hydrogen, halo (for example fluoro) or $NH_2$.

Preferably $R^{1a}$ and $R^{1b}$ are independently hydrogen or fluoro.

Preferably $R^2$ is a group

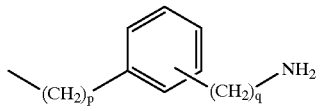

or

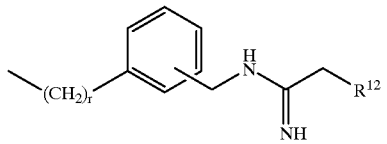

wherein p, q and r are independently 0, 1 or 2 and $R^{12}$ is as hereinbefore defined.

One embodiment of the present invention provides a compound of formula (IA)

(IA)

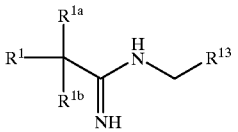

wherein $R^1$, $R^{1a}$ and $R^{1b}$ are as hereinbefore defined, and $R^{13}$ is a $C_{1-13}$ hydrocarbyl group which may optionally contain one or two heteroatoms, the group $R^{13}$ being optionally substituted by one or two groups which may be the same or different, and are selected from halo, ZR7 or a group

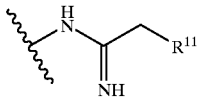

wherein Z, $R^7$ and $R^{11}$ are as hereinbefore defined.

A second aspect of the present invention provides a compound of formula (IB)

(IB)

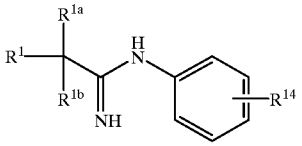

wherein $R^1$, $R^{1a}$ and $R^{1b}$ are as hereinbefore defined, and $R^{14}$ represents one or two substituents on the phenyl ring independently selected from halo, $ZR^7$ or a group

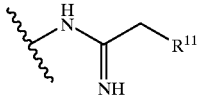

wherein Z, $R^7$ and $R^{11}$ are as hereinbefore defined, or $R^{14}$ is a $C_{1-8}$ hydrocarbyl group optionally containing one or two heteroatoms, and optionally substituted by one or two groups which may be the same or different, and are selected from halo, $ZR^7$ or a group

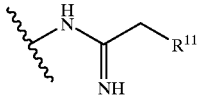

wherein Z, $R^7$ and $R^{11}$ are as hereinbefore defined.

In a third aspect the invention provides a compound of the formula IC:

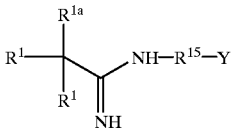

wherein $R^1$, $R^{1a}$ and $R^{1b}$ are as hereinbefore defined;

$R^{15}$ is a bond or $CH_2$; and

Y is $C_{1-6}$ hydrocarbyl group, phenyl, indanyl or a 5–10 membered heterocyclic group containing 1 or 2 heteroatoms independently selected from O, N, and S;

wherein Y is optionally substituted by one or more groups independently selected from halo, amino, cyano, nitro, hydroxy, $C_{1-6}$ hydrocarbyl optionally substituted by hydroxy, $C_{1-6}$ alkoxy, $C_{1-6}$ thioalkyl, $CF_3$, $N_3$, a group:

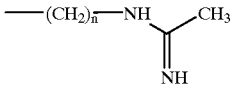

wherein n is as hereinbefore defined, $C(O)_{m'}B$ or $S(O)_{n'}B$ wherein m' and n' are as hereinbefore defined and B is amino or $C_{1-6}$ alkyl , a group:

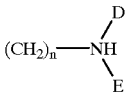

wherein n is as hereinbefore defined and D and E are independently hydrogen, hydroxy, amino, $C_{1-6}$ alkyl, —$CNHCH_3$, —$CO_2{}^tBu$, or a 5–10 membered heterocyclic group containing 1 or 2 heteroatoms independently selected from O, N or S, a group:

$$—(CH_2)_n—NH—(CH_2)_{n'}A$$

wherein n and n' are as hereinbefore defined and A is phenyl, or a 5- or 6-membered heterocyclic group containing 1 or 2 heteroatoms selected from O, N and S optionally substituted by

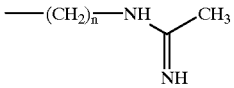

a group:

$$—(CH_2)_n—G$$

wherein n is as hereinbefore defined and G is —$CO_2H$, —$CO_2C_{1-6}$ alkyl or a 5–10 membered heterocyclic group containing 1 or 2 heteroatoms independently selected from O, N or S optionally substituted by amino, $CNHNH_2$ and $CH_2SCNHNH_2$.

In a preferred embodiment of this aspect of the invention a compound of the formula IC is provided wherein:

$R^{15}$ is a bond or $CH_2$;

Y is $C_{1-6}$ hydrocarbyl, phenyl, indanyl or a 5–10 membered heterocyclic group containing 1 or 2 heteroatoms independently selected from O, N or S;

wherein Y is optionally substituted by one or more groups independently selected from halo, amino, cyano, nitro, hydroxy, $C_{1-6}$ hydrocarbyl optionally substituted by hydroxy, $C_{1-6}$ thioalkyl, a group:

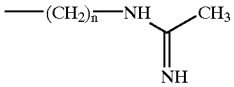

wherein n is as hereinbefore defined, $C(O)_{m'}B'$ or $S(O)_{n'}B'$ wherein m' and n' are as hereinbefore defined and B' is amino or $C_{1-6}$ alkyl, a group:

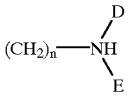

wherein n is as hereinbefore defined and D and E are independently hydrogen, hydroxy, amino, $C_{1-6}$ alkyl, —$CNHCH_3$, —$CO_2{}^tBu$, or a 5–10 membered heterocyclic group containing 1 or 2 heteroatoms independently selected from O, N or S, a group:

$$—(CH_2)_n—NH—(CH_2)_{n'}—A$$

wherein n and n' are as as hereinbefore defined and A is phenyl, or a 5- or 6-membered heterocyclic group containing 1 or 2 heteroatoms selected from O, N and S optionally substituted by

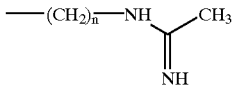

a group:

$$—(CH_2)_n—G$$

wherein n is as hereinbefore defined and G is a 5–10 membered heterocyclic group containing 1 or 2 heteroatoms independently selected from O, N or S optionally substituted by amino, $CNHNH_2$ and $CH_2SCNHNH_2$.

In a particularly preferred embodiment of this aspect of the invention the invention provides a compound of the formula IC wherein:

$R^{15}$ is a bond or $CH_2$:

Y is $C_{1-6}$ hydrocarbyl, phenyl, indanyl or a 5–10 membered heterocyclic group containing 1 or 2 heteroatoms independently selected from O, N or S;

wherein Y is optionally substituted by one or more groups independently selected from amino, $C_{1-6}$ hydrocarbyl optionally substituted by hydroxy, a group:

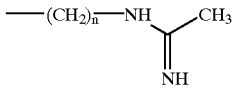

wherein n is as hereinbefore defined, a group:

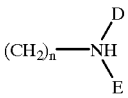

wherein n is as hereinbefore defined and D and E are independently hydrogen, hydroxy, amino, $C_{1-6}$ alkyl, —$CNHCH_3$, or a 5–10 membered heterocyclic group containing 1 or 2 heteroatoms independently selected from O, N or S, a group:

$$—(CH_2)_n—NH—(CH_2)_{n'}—A$$

wherein n and n' are as hereinbefore defined and A is phenyl, or a 5- or 6-membered heterocyclic group containing 1 or 2 heteroatoms selected from O, N and S optionally substituted by

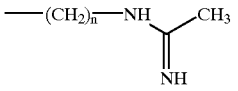

a group:

$$—(CH_2)_n—G$$

wherein n is as hereinbefore defined and G is a 5–10 membered heterocyclic group containing 1 or 2 heteroatoms independently selected from O, N or S, $CNHNH_2$ and $CH_2SCNHNH_2$.

A preferred group of compounds within formula (IC) are those where $R^{15}$ is a bond. Such compounds are selective inhibitors of the neuronal NOS. Particularly preferred compounds within this sub-group are those where Y is optionally substituted phenyl or a optionally substituted 5–10 membered heterocyclic group containing 1 or 2 heteroatoms independently selected from O, N or S. Examples of such compounds include:

N-(3-(Hydroxymethyl)phenyl)Acetamidine;
N-(3-(Aminomethyl)phenyl)acetamidine;
N-(3-(( 1,2,3,4-tetrahydroisoquinol-2-yl)methyl)phenyl)-acetamidine;
N-(3-((Methylamino)methyl)phenyl)acetamidine;
N-(Dimethylamino)methyl)phenyl)acetamidine;
N-(3-Morpholinomethyl)phenyl)acetamidine;
N-(3-(Aminomethyl)phenyl)-2-fluoroacetamidine;
N-(3-(2-Aminoethyl)phenyl)acetamidine; and
N-(1,2,3,4-Tetrahydroisoquinolin-7-yl)acetamidine;
and salts thereof.

A second preferred group of compounds within formula (IC) are those where $R^{15}$ is $—CH_2—$. This group of compounds are selective inhibitors of the inducible NOS. Particularly preferred compounds within this subgroup are those where Y is is optionally substituted phenyl, indanyl or a optionally substituted 5–10 membered heterocyclic group containing 1 or 2 heteroatoms independently selected from O, N or S. Examples of such compounds include:

N-(3-(aminomethyl)benzyl)acetamidine;
N-(4(aminomethyl)benzyl)acetamidine;
N-(3-(Aminomethyl)benzyl)-2-fluoroacetamidine;
N-(3-(Aminomethyl)benzyl)-2-aminoacetamidine;
N-[[6-(Aminomethyl)-2-pyridyl]methyl]acetamidine;
N-(3-(Aminomethyl)benzyl)-2,2,2-trifluoroacetamidine;
N-((1H-Indazol-6-yl)methyl)acetamidine; and
N-(3-Amino-5-indanyl)methyl)acetamidine;
and salts thereof.

Especially preferred compounds within this group include:

N-(3-(aminomethyl)benzyl)acetamidine;
N-(4-(aminomethyl)benzyl)acetamidine;
N-(3-(Aminomethyl)benzyl)-2-fluoroacetamidine;
N-(3-(Aminomethyl)benzyl)-2-aminoacetamidine;
N-[[6-(Aminomethyl)-2-pyridyl]methyl]acetamidine;
N-((1H-Indazol-6-yl)methyl)acetamidine; and
N-(3-Amino-5-indanyl)methyl)acetamidine;
and salts thereof.

Preferred compounds of formula (I) or (IC) include:

N-(3-(aminomethyl)benzyl)acetamidine;
N-(3-(aminomethyl)benzyl)-2-fluoroacetamidine;
N-(4-(aminomethyl)benzyl)acetamidine;
N-(4-aminobutyl)acetamidine;
N-(5-aminopentyl)acetamidine;
N-(6-aminohexyl)acetamidine;
N-(7-aminoheptyl)acetamidine;
N,N'-(1,3-phenylenebis (methylene))bis(acetamidine);
N,N'-(1,4-phenylenebis (methylene))bis(acetamidine);
N,N'-(1,3-phenylene (diethylene))bis(acetamidine);
N,N'-(1,4-phenylene (diethylene))bis(acetamidine);
N-(3-(aminomethyl)benzyl)-2-methoxyacetamidine;
2-Amino-N-(3-aminomethyl)benzyl)acetamidine;
N-(3-(hydroxymethyl)phenyl)acetamidine;
N-(3-(aminomethylphenyl)acetamidine;
N-(3-(Aminomethyl)phenyl)acetamidine;
N-(3-(Aminomethyl)phenyl)-2-fluoroacetamidine; and
N-(3-Amino-5-indanyl)methyl)acetamidine
and salts thereof.

Especially preferred compounds include N-(3-(aminomethyl)benzyl)acetamidine;
N-(3-(aminomethyl)benzyl)-2-fluoroacetamidine;
N-(3-(Aminomethyl)phenyl)acetamidine;
N-(3-(Aminomethyl)phenyl)-2-fluoroacetamidine; and
N-((3-Amino-5-indanyl)methyl)acetamidine
and salts thereof.

By the term "hydrocarbyl" is meant a group containing only hydrogen and carbon atoms, and may contain double and/or triple bonds and which may be straight, branched, cyclic or aromatic in nature.

The term "heteroatom" has the meaning known to one skilled in the art and includes nitrogen, oxygen and sulphur atoms.

By the term "halo" is meant fluoro, chloro, bromo, or iodo, and preferably fluoro.

The compounds of formula (I) may include a number of asymmetric centres in the molecule depending on the precise meaning of the various groups, and formula (I) is intended to include all possible isomers.

As hereinbefore mentioned, the compounds of formula (I) have activity as inhibitors of NO synthase and accordingly a further aspect of the present invention provides a compound of formula (I) for use in medicine.

A yet further aspect provides the use of a compound of the invention in the manufacture of a medicament for the treatment of a condition requiring inhibition of NO synthase. More specifically, there is provided the use of a compound of the invention for the manufacture of a medicament for the treatment of a condition where there is an advantage in inhibiting an NO synthase isoenzyme with little or no inhibition of the other isoenzymes.

In another aspect, the present invention provides a method of treating a condition requiring inhibition of NO synthase, in particular the inhibition of one NO synthase isoenzyme with little or no inhibition of the other isoenzymes, comprising administering to a mammal in need thereof an effective amount of a compound of the invention or a pharmaceutically acceptable salt thereof.

In a further aspect, there is provided the use of a compound of the invention or salt thereof in the manufacture of a medicament for the treatment of shock states resulting from overproduction of NO by iNOS such as septic shock, or shock caused by fulminant hepatic failure or by therapy with cytokines such as TNF, IL-1 and IL-2 or therapy with cytokine-inducing agents, for example 5, 6-dimethylxanthenone acetic acid.

Other conditions where there is an advantage in selectively inhibiting iNOS include a wide range of auto-immune and/or inflammatory diseases, such as those of the joint (e.g. rheumatoid arthritis, osteoarthritis), of the gastrointestinal tract (e.g. ulcerative colitis and other inflammatory bowel diseases, gastritis and mucosal inflammation resulting from infection), of the lung (adult respiratory distress syndrome, asthma), of the heart (myocarditis), of the nervous tissue (e.g. multiple sclerosis), of the pancreas (e.g. diabetes melitus), of the kidney (e.g. glomerulonephritis), of the skin (e.g. dermatitis, psoriasis, urticaria) as well as of transplanted organs (rejection) and multi-organ diseases (e.g. systemic lupus erythematosis). Furthermore there is evidence for overproduction of NO by iNOS in atherosclerosis. Therefore, a yet further aspect of the present invention provides the use of a compound of formula (I) or salt thereof in the manufacture of a medicament for use in treating the above conditions.

Inhibition of neuronal NOS is of benefit in the treatment of diseases of the nervous system due to over production of NO by this isoenzyme, particularly the treatment of cerebral ischemia. Other diseases include CNS trauma, epilepsy, AIDS dementia, chronic neurodegenerative disease and chronic pain, and conditions in which non-adrenergic non-cholinergic nerve may be implicated such as priapism, obesity and hyperphagia. Accordingly the present invention also provides the use of a compound of formula (I) or a salt thereof in the manufacture of a medicament for use in treating the above conditions.

Furthermore inhibition of NO synthase may be of advantage in preventing the lymphocyte loss associated with HIV infection, and in reducing tumour growth and metastasis.

Inhibition of both iNOS and nNOS may be of benefit in the treatment of certain conditions where both isoenzymes play a role, for example CNS conditions such as cerebral ischemia.

As used herein, reference to "treatment" of a patient is intended to include prophylaxis; the term "mammal" is intended to include a human or an animal.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic and isethionic acids. Salts of compounds of formula (I) can be made by reacting the appropriate compound in the form of the free base with the appropriate acid.

Whilst it may be possible for the compounds of the present invention to be administered as the raw chemical, it is preferable to present them as a pharmaceutical formulation. According to a further aspect, the present invention provides a pharmaceutical formulation comprising a compound of formula (I) or a pharmaceutically acceptable salt or solvate thereof, together with one or more pharmaceutically acceptable carriers therefor and optionally one or more other therapeutic ingredients, for example an antibiotic, and/or a volume replacement liquid. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general the formulations are prepared by uniformly and intimately bringing into association the active ingredient with liquid carriers or finely divided solid carriers or both and then, if necessary shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, water-for-injection, immediately prior to use. Alternatively, the formulations may be presented for continuous infusion.

Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

For each of the aforementioned conditions, the compounds of the invention may be administered orally or via injection at a dose of from 0.1 to 250 mg/kg per day. The dose range for adult humans is generally from 5 mg to 17.5 g/day, preferably 5 mg to 2 g/day and most preferably 10 mg to 1 g/day, for example 15 mg to 600 mg/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However the dose employed will depend on a number of factors, including the age and sex of the patient, the precise disorder being treated, and its severity. Also the route of administration may vary depending on the condition and its severity. Certain compounds of formula (I) are novel, and accordingly a further aspect of the present invention provides a process for the preparation of a compound of formula (I) as hereinbefore defined.

Thus, compounds of formula (I) or protected derivatives thereof may be prepared by the reaction of an amine of formula (II)

$$H_2N—R^2$$

or a protected derivative thereof wherein $R^2$ is as hereinbefore defined, with a 1-benzylthioethaniminium derivative of formula (III)

(III)

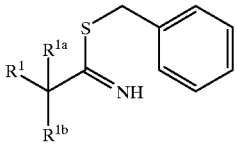

•HX wherein $R^1$, $R^{1a}$ and $R^{1b}$ are as hereinbefore defined followed by deprotection if necessary. The reaction may be carried out in a polar solvent, for example a $C_{1-4}$ alkanol such as ethanol at a non-extreme temperature of from −20° C. to 100° C. such as 0° C. The 1-benzylthioethaniminium derivative of formula (III) is suitably a halide derivative, preferably a chloride or bromide. Deprotection may be carried out by methods well known to those skilled in the art, for example by methods described in Greene, T. W.; Wuts, P. G. M. (1991) Protective Groups in Organic Synthesis, p 327–330, John Wiley, New York.

Compounds of formula (III) may be prepared by the S-alkylation of thioamide compounds of formula (IV)

(IV)

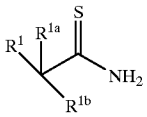

wherein $R^1$, $R^{1a}$and $R^{1b}$ are as hereinbefore defined with benzyl bromide or chloride as described previously (Takido, Y., Itabashi, K. Synthesis 1987, p 817–819). The reaction may be carried out in a solvent such as chloroform at non-extreme temperatures of from 0° C. to 200° C., such as refluxing chloroform.

Compounds of formula (II) and (IV) are commercially available or may be prepared by methods known to a person skilled in the art.

Where Y is an indanyl group, the following synthetic schemes can be used for the preparation of such compounds:

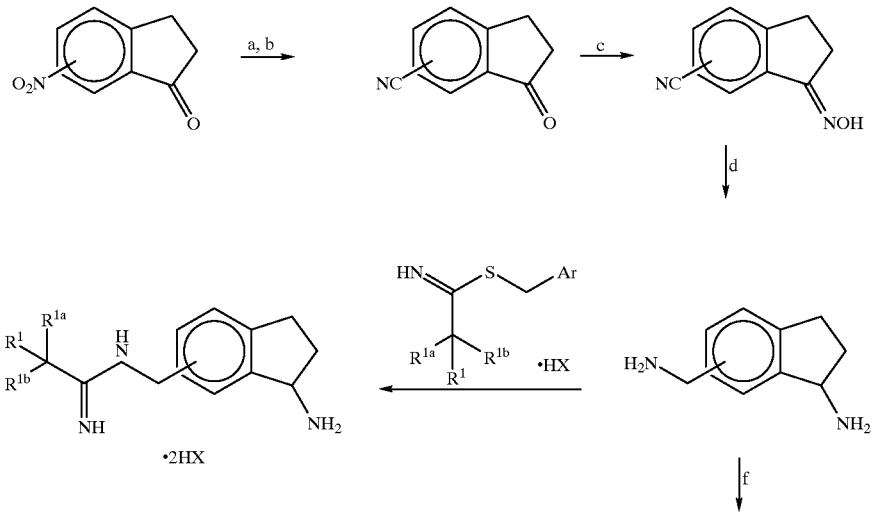

-continued

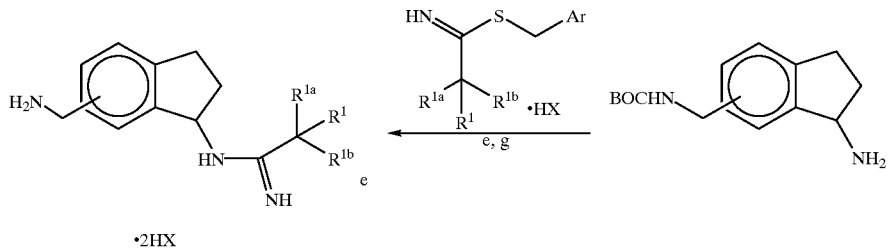

Reagents: (a) EtOH, $H_2$/Pd/C; (b) $NANO_2$, then CuCN; (c) pridine, $BnONH_2$.HCl; (d) $BH_3$.THF; (e) EtOH, 20° C.; (f) $(BOC)_2$—O, MeOH/$CH_2Cl_2$, $Et_3N$; (g)HCl, Dioxane.

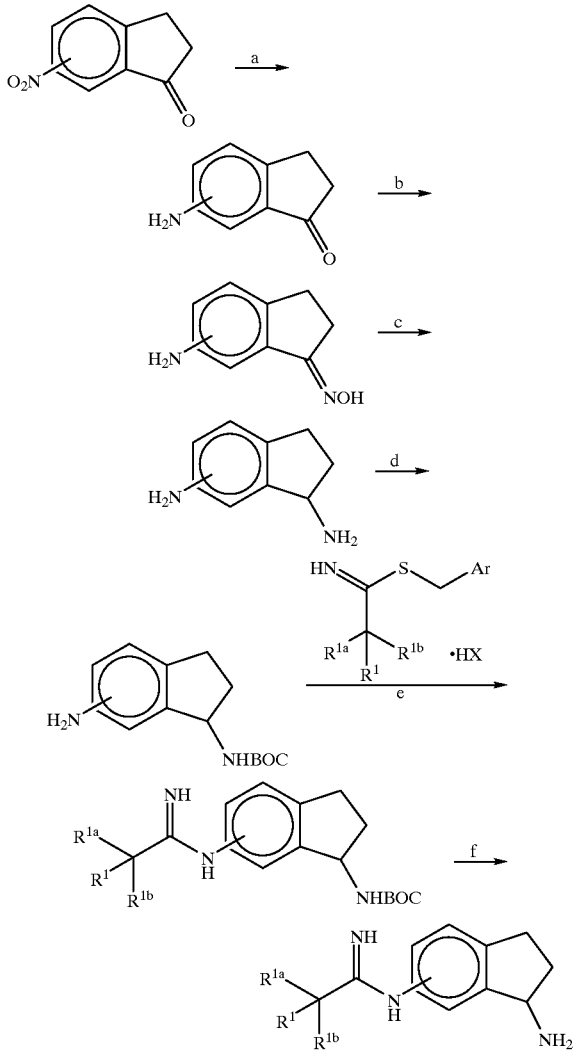

Reagents: (a) EtOH, $H_2$Pd/C; (b) pyridine, $BnONH_2$.HCl; (c) $BH_3$.THF; (d) $(BOC)_2$—O, MeOH/$CH_2Cl_2$, $Et_3N$; (e) EtOH, 20° C.; (f) HBr/AcOH.

An additional method for the preparation of compounds of the invention involves the conversion of an azide into an amidine utilising a one-pot method involving triphenylphosphine reduction followed by in situ amidination of the intermediate amine. A further refinement of the method involves the use of polymer-supported triphenylphosphine, the byproduct oxide of which can be readily filtered from the reaction mixture.

Preferred features of each aspect of the invention are as for each other aspect, mutatis mutandis.

THE PRESENT INVENTION WILL NOW BE DESCRIBED BY WAY OF EXAMPLE ONLY:

INTERMEDIATE A

Preparation of S-Benzylthioacetimidate Hydrochloride (Takido, Y.; Itabashi, K. Synthesis 1987, p 817–819)

A solution of thioacetamide (60.0 g) and 91.9 ml benzyl chloride in 600 ml chloroform was stirred at reflux for 14 h. Upon cooling to 0° C., the white solids were collected via filtration and dried in vacuo to yield 101 g of a white solid. Dilution of the filtrate with 400 ml $Et_2O$ and filtration provided an additional 46 g of a pale yellow solid. $^1H$ NMR (300 MHz, DMSO) δ 7.5–7.3 (m, 5H), 4.66 (s, 2H), 2.67 (s,3H).

The following intermediates were prepared by an analogous method:

B S-Benzylthioacetirndate Hydrobromide: from thioacetamide and benzyl bromide. $^1H$ NMR (200 MHz, DMSO) δ 2.65 (3H, s), 4.63 (2H, s), 7.51–7.31 (5H, m).

C S-(2-Naphthylmethyl)thioacetimidate Hydrobromide: from thioacetamide and 2-(bromomethyl)naphthalene. $^1H$ NMR (200 MHz, DMSO) δ 11.9 (br s, 1H), 8.04–7.92 (m, 4H), 7.6–7.55 (m, 3H), 4.8 (s, 2H), 2.68 (s,3H).

D S-Benzyl-2-fluorothioacetimidate Hydrobromide: from fluorothioacetamide and benzyl bromide. $^1H$ NMR (300 MHz, DMSO) δ 7.5–7.3 (m, 5H), 4.66 (s, 2H), 2.67 (s,3H).

E S-(2-Naphthylmethyl)-2-fluorothioacetimidate Hydrobromide: from fluorothioacetamide and 2-(bromomethyl) naphthalene. $^1H$ NMR (200 MHz, DMSO) δ 7.91–7.82 (m, 4H), 7.65–7.48 (m, 3H), 4.73 (d, J=47.2 Hz, 2H), 3.9 (s,3H).

F S-(2-Naphthylmethyl)-2,2-difluorothioacetimidateHydrobromide: from difluorotdioacetamide and 2-(bromomethyl)naphthalene. (Crude)

G S-Benzyl-2-methoxythioacetimidate Hydrobromide: from 2-methoxy-thioacetamide and benzyl bromide. $^1H$ NMR (200 MHz, DMSO) δ 3.42 (3H,s), 4.61 (2H,s), 4.67 (2H, s), 7.44 (5H, m).

H S-(2-Naphthylmethyl)-2-(thiomethyl)thioacetimidate Hydrobromide: from 2-(thiomethyl)thioacetamide and 2-(bromomethyl)naphthalene. $^1H$ NMR (200MHz, DMSO; D2O) δ 2.09 (3H, s), 3.89 (2H,s), 4.67 (2H, s), 7.91–7.44 (7H, m).

I S-Benzyl-2-tertbutylcarbamoylthioacetimidate Hydrobromide: from 2-(tert-butylcarbamoyl)thioacetamide and benzyl bromide. $^1H$ NMR (200 MHz,DMSO) δ 1.40 (9H, s), 4.27 (2H, d), 4.56 (2H, s), 7.42 (5H, m), 7.79 (1H, t).

J S-Benzylthiopropionimidate Hydrobromide: from benzyl bromide and thiopropionamide. $^1H$ NMR (400 MHz, DMSO) δ 7.46–7.32 (m, 5H), 4.59 (s,2H), 2.83 (d, J=7.5 Hz, 2H), 1.21 (t, J=7.5 Hz, 3H).

EXAMPLE 1

Preparation of N-(3-aminomethyl)benzyl) acetamidine

Preparation of Intermediate tert-butyl-N-(3-(aminomethyl) benzyl)carbamate 10 g (73.42 mmol) of m-xylenediamine was added to 5.1 ml (36.71 mmol) of triethylamine and 200 ml of anhydrous methanol. To this solution at 0° C. was added dropwise over 60 minutes a solution of 8.0 g (36.71 mmol) of di-tert-butyldicarbonate in 60 mL of tetrahyrofuran (anhydrous). The solution was stirred an additional two hours at 0° C., filtered, and concentrated to dryness. The crude material was purified by silica gel chromatography (230–400 mesh silica gel, 250 g). The column was initially eluted with 20% methanol in methylene chloride, then methylene chloride. The crude product was then loaded onto the column and eluted with methanol/ methylene chloride/ ammonium hydroxide ( 5/95/0.5 to 15/85/0.5). Product fractions were concentrated to yield 5.28 g (30%) of a thick, viscous yellow oil. TLC: 10% methanol in methylene chloride (0.5% ammonium hydroxide) on silica gel, Rf=0.7. Mass Spectrum (CI) 237.1 ($MH^+$, 100%), $^1H$ NMR (200 MHz, CDCl3) δ 7.35–7.15 (m, 4H), 4.9 (br. s, 1H), 4.3 (m, 2H), 3.85 (m, 2H), 1.6 (s, 3H).

Amidine Synthesis: Preparation of Intermediate tert-butyl N-(3-((acetimidoyl)aminomethyl)benzyl)-carbamate To a solution of 2.6 g (11.0 mmol) tert-butyl N-(3-(aminomethyl) benzyl carbamate in 25 ml of absolute ethanol at 0° C. was added 2.22 g (11.0 mmol) of intermediate A. The solution was stirred for three hours and concentrated to dryness. The residue was partitioned between ether (100 ml) and water (100 ml). The aqueous was extracted with ether (50 ml) and freeze-dried to yield 3.28 g (95%) of white solid carbamate hydrochloride as product. $^1H$ NMR (200 MHz, DMSO) δ 7.4–7.3 (m, 1H), 7.24–7.16 (m, 3H), 4.46 (s, 2H), 4.13 (s, 2H), 2.21 (s, 3H), 1.4 (s, 9H). Mass Spectrum (CI) 278.1 ($MH^+$, 100%).

Deprotection of Intermediate tert-butyl N-(3-((Acetimidoyl) aminomethyl)benzyl)-carbamate Solid tert-butyl N-(3-((acetimidoyl)aminomethyl)benzyl) carbamate (3.0 g, 9.6 mmol) was suspended into 150 ml anhydrous dioxane. 4N Hydrochloric acid in dioxane solution (20 ml) was added at 20° C. The mixture was stirred for 24 hours at 20° C. After diluting with 200 ml ether, the white solids were collected by filtration and dried under vacuum at 100° C. to yield 2.34 g (98%) of N-(3-(aminomethyl) benzyl)-acetamidine. $^1H$ NMR (200 MHz, D2O) δ 7.52–7.35 (m, 4H), 4.49 (s, 2H), 4.16 (s, 2H), 2.25 (s, 3H). Mass Spectrum (CI) 177.9 ($MH^+$, 100%).

EXAMPLE 2

Preparation of N-(3-(Aminomethyl)benzyl)-2-fluoroacetamidine

To a solution of 14 g (59.24 mmol) tert-butyl N-(3-(aminomethyl) benzyl)carbamate in 100 ml ethanol at 0° C. was added 18.8 g (71.1 mmol) of intermediate B. The solution was concentrated after 14 h to a thick oil, stirred vigorously, and 200 ml of ether was added. The residue that separates was washed several times with ether. The resulting solid was stirred in 250 ml of acetic acid and 25 ml of 30% HBr in acetic acid solution. After stirring 30 minutes. 500 ml of ether was added and the solids were collected by filtration and dried to yield 21.55 g (100%) of N-(3-(Aminomethyl) benzyl)-2-fluoroacetamidine as a white solid. A 2.0 g sample was recrystallized from MeOH/EtOAc to yield 1.43 g of a white solid. Mass spectrum (CI) 196.0 ($MH^+$, 76%). $^1H$ NMR (200 MHz, DMSO) δ 7.52–7.38 (m, 4H), 5.42 (d, J=45.3 Hz, 2H), 4.6 (s, 2H), 4.07 (s, 2H).

EXAMPLE 3

Preparation of N-(4-(Aminomethyl)benzyl) acetamidine

Prepared from tert-butyl N-(4-(aminomethyl)benzyl carbamate and intermediate A by the method of example 1 except that the crude deprotection product was freeze-dried from 25 ml water. Mass spectrum (CI) 178 ($MH^+$, 100%). $^1H$ NMR (200 MHz, D2O) δ 7.5–7.35 (m, 4H), 4.5 (s, 2H), 4.15 (s, 2H), 2.15 (s, 3H).

EXAMPLE 4

Preparation of N-(3-(Aminomethyl)benzyl)-2-methoxyacetamidine

The intermediate tert-butyl N-(3-((2-methoxyacetimidoyl) aminomethyl)benzyl)carbamate (360 mg) prepared from tert-butyl N-(3-(aminomethyl)benzyl carbamate and intermediate G analogous to example 1 was deprotected in trifluoroacetic acid at 20° C. for 16 h. The crude product was purified by C18 reverse phase chromatography eluting with water (0.1% trifluoroacetic acid) to yield 150 mg of N-(3-(Aminomethyl)benzyl)-2-methoxyacetamidine as a yellowed, viscous oil (freeze-dried). Mass spectrum (CI) 208.0 ($MH^+$, 100%). $^1H$ NMR (200 MHz, D2O) δ 7.5–7.3 (m, 4H), 4.57 (s, 2H), 4.37 (s, 2H), 4.15 (s, 2H), 3.44 (s, 3H).

EXAMPLE 5

Preparation of N-(3-(Aminomethyl)benzyl)-2-aminoacetamidine

Prepared from 430 mg of tert-butyl N-(3-(aminomethyl) benzyl carbamate and intermediate I analogous to example 4. The freeze-dried fractions left 640 mg of a yellowed viscous oil. Mass spectrum (CI) 193.1 ($MH^+$, 100%). Capillary electrophoresis produced a single peak.

EXAMPLE 6

Preparation of N-(4-Aminobutyl)acetamidine

Prepared from 0.98 g (5.23 mmol) N-Boc-1,4-diaminobutane and intermediate B analagous to example 1. The product residue was purified by preparative reverse phase (C18) chromatography eluting with a methanol/water/ trifluoroacetic acid gradient (5/95/0.1 to 90/10/0.1) to yield 0.76 g of pale yellow N-(4-aminobutyl)acetamidine. Capillary electrophoresis gave a single peak (50 mm×40 cm fused silica capillary, 5.5 minutes). Mass spectrum (CI) 130.0 ($MH^+$, 95%). $^1H$ NMR (300 MHz, D2O) δ 3.15 (m, 2H), 2.89 (m, 2H), 2.08 (s, 3H), 1.62–1.55 (m, 4H).

EXAMPLE 7

Preparation of N-(5-Aminopentyl)acetamidine

Prepared from 0.97 g (4.8 mmol) N-Boc-1,5-diaminopentane analogous to example 6. Capillary electrophoresis gave a single peak (50 mm×40 cm fused silica capillary, 5.9 minutes). Mass spectrum (CI) 144.0 ($MH^+$, 100%). $^1H$ NMR (300 MHz, D2O) δ 3.12 (m, 2H), 2.85 (m, 2H), 2.08 (s, 3H), 1.6–1.5 (m, 4H), 1.35–1.25 (m, 2H).

EXAMPLE 8

Preparation of N-(6-Aminohexyl)acetamidine

To a 0° C. stirred solution of 1.0 g (4.62 mmol) of N-Boc-1,6-diaminohexane in 30 ml ethanol was added 0.86 g (4.62 mmol) of intermediate B. After two hours the solution was concentrated, diluted with water (50 ml), and extracted with ether twice. The aqueous phase was freeze-dried to yield 0.9 g of white sticky solid tert-butyl N-(6-((acetimidoyl) amino)hexyl)carbamate intermediate. A suspension of the carbamate above (0.88 g, 3 mmol) in 15 ml dioxane and 7.5 ml trifluoroactic acid was treated with 10 ml (40 mmol) of 4N hydrochloric acid in dioxane solution with stirring overnight. The mixture was diluted with ether (50 ml) and the solids were isolated by filtration to provide 0.7 g N-(6-aminohexyl)acetamidine as a white solid (66% yield from N-Boc-1,6-diaminohexane). M.P.=163°–164° C. Mass spectrum (CI) 158.1 ($MH^+$, 100%).

EXAMPLE 9

Preparation of N-(7-Aminoheptyl)acetamidine

Prepared from N-Boc-1,7-diaminohexane (1.0 g, 4.34 mmol) by the method of example 8 to yield 0.76 g of the title compound as a white solid. M.P.=165°–168° C. Mass spectrum (CI) 172.1 ($MH^+$, 100%). $^1H$ NMR (300 MHz, D2O) δ 3.16 (t, J=7.0 Hz, 2H), 2.9 (t, J=7.5 Hz, 2H), 2.11 (s, 3H), 1.59–1.5 (m, 4H), 1.28 (br s, 6H).

EXAMPLE 10

Preparation of N,N'-(1,3-Phenylenebis(methylene)) bis(acetamidine)

To a solution of 1.0 g (7.34 mmol) m-xylenediamine in 75 ml ethanol at 0° C. was added 3.7 g (15.0 mmol) of solid intermediate B. The solution was stirred at 0° C. for two hours and concentrated. The residue was taken into 50 ml of water and extracted twice with ether (2×50 ml). The aqueous solution was freeze-dried to provide a quantitative yield of N,N'-(1,3-phenylenebis(methylene))bis(acetamidine) bis-hydrobromide as a white solid (2.81 g). Mass spectrum (CI) 219.0 ($MH^+$, 26%). $^1H$ NMR (300 MHz, D2O) δ 7.3 (m, 1H), 7.2 (m, 3H), 4.35 (s, 4H), 2.15 (s, 6H).

Examples 11–13 were prepared from the appropriate diamines by methods analogous to example 10:

EXAMPLE 11

N,N'-(1,4-Phenylenebis(methylene))bis(acetamidine)

Mass spectrum (FAB) 219.3 ($MH^+$, 100%). $^1H$ NMR (300 MHz, D2O) δ 7.45 (s, 4H), 4.46 (s, 4H), 2.2 (s, 6H).

EXAMPLE 12

N,N'-(1,3-Phenylene(diethylene))bis(acetamidine)

Mass spectrum (FAB) 247.2 ($MH^+$, 100%). $^1H$ NMR (200 MHz, D2O) δ 7.35–7.15 (m, 4H), 3.50 (t, J=6.8 Hz, 4H), 2.9 (t, J=6.9 Hz, 4H), 2.1 (s, 6H).

EXAMPLE 13

N,N'-(1,4-Phenylene(diethylene))bis(acetamidine)

Mass spectrum (CI) 247 ($MH^+$, 25%). $^1H$ NMR (300 MHz, D2O) δ 7.16 (s, 4H), 3.40 (t, J=6.8 Hz, 4H), 2.81 (t, J=6.8 Hz, 4H), 2.04 (s, 6H).

EXAMPLE 14

Preparation of N-(3-(hydroxymethyl)phenyl) acetamidine

Prepared from 1.23 g (10 mmol) 3-aminobenzyl alcohol and 2.22 g (11.0 mmol) of intermediate A by the method of example 1 to provide a white solid (2.0 g, 100% yield). Mass spectrum (CI) 165.0 ($MH^+$, 100%). Capillary zone electrophoresis on a fused silica column (75 microns×40 cm) at pH=2 gave a 7.78 minute retention time, 99.3% purity. $^1H$ NMR (300 MHz, D2O) δ 7.4 (t, J=7.7 Hz, 1H), 7.3 (d, J=7.4 Hz, 1H), 7.18 (s, 1H), 7.13 (d, J=7.9 Hz, 1H), 4.52 (s, 2H), 2.26 (s, 3H).

EXAMPLE 15

Preparation of N-(3-(Aminomethyl)phenyl) acetamidine

To a stirred solution of 2.5 g (13.25 mmol) 3-nitrobenzylamine hydrochloride and 8.5 ml (30 mmol) of triethylamine in 75 ml anhydrous methanol and 25 ml anhydrous tetrahydrofuran was added 3.19 g (14.5 mmol) di-tertbutyl dicarbonate. The solution was filtered after 14 hours, concentrated, and purified by silica gel chromatography to yield 3.3 g (100%) of protected intermediate (silica gel Rf=0.45, 30% ethyl acetate in hexanes). A solution of 3.1 g (12.29 mmol) of this intermediate was hydrogenated for 90 minutes under 50 psi hydrogen in 75 ml methanol in the presence of 1 g 10% palladium on carbon. The mixture was filtered and concentrated to an oil (2.65 g). This oil was taken into 30 ml ethanol (0° C.) and 2.48 g (12.3 mmol) intermediate A was added. After 3 hours, the solution was concentrated, partitioned between 100 ml ether and 40 ml water, and the aqueous phase was washed with ether (100 ml) and freeze-dried to a white solid (3.5 g, 95% yield). Mass spectrum (CI) 264.1 ($MH^+$, 100%). To a suspension of 2.0 g (6.67 mmol) of this solid in 20 mL dioxane was added 30 ml of 4N hydrochloric acid in dioxane solution. The suspension was stirred for two hours, diluted with 150 ml ether, and filtered. The solids recovered were dried under vacuum to yield 1.36 g (86%) of the title compound N-(3-aminomethylphenyl)acetamidine dihydrochloride. Mass spectrum (CI) 164.0 ($MH^+$, 100%). Capillary zone electrophoresis on a fused silica column (75 microns×40 cm) at pH=2.1 gave a 5.06 minute retention time, 97.6% purity. $^1H$ NMR (300MHz, DMSO) δ 7.6–7.5 (m, 3H), 7.3 (m, 1H), 4.03 (s, 2H), 2.36 (s, 3H).

EXAMPLE 16

Preparation of N-[[6-(Aminomethyl)-2-pyridyl] methyl]acetamidine

Prepared from 1.5 g (10.9 mmol) Bis-2,6-(aminomethyl) pyridine ( synthesized by standard methods from 2,6-pyridinedimethanol via bromination with carbon tetrabromide and triphenylphosphine, bis-azide formation with sodium azide in dimethylformamide, and catalytic hydrogenation to the diamine with palladium on carbon) and intermediate B analogous to example 10. The crude product was purified by preparative reverse phase HPLC (C18) eluting with a gradient of methanol/water/trifluoroacetic acid (10/90/0.1 to 90/10/0.1) and freeze-dried to yield N-[[6-(aminomethyl)-2-pyridyl]methyl]acetamidine (clear, colorless, viscous oil, 130 mg). Mass spectrum (CI) 179.0 ($MH^+$, 100%).

EXAMPLE 17

PreparationofN-(2-(5-((acetimidoylamino)methyl)-2-thienyl)ethyl)acetamidine

Prepared from 2-(2-Aminoethyl)-5-(aminomethyl) thiophene and intermediate B analogous to example 10.

Mass Spectrum (FAB) 239.1 ($MH^+$). $^1H$ NMR (200 MHz D2O) δ 6.95 (d, J=3.5 Hz, 1H), 6.81 (d, J=3.4 Hz, 1H), 4.58 (s, 2H), 3.52 (t, J=6.6 Hz, 2H), 3.1 (s, 3H), 2.14 (s, 3H).

EXAMPLE 18

Preparation of N-(3-(5-(2-(Acetimidoylamino) ethyl)-2-thienyl)propyl)acetamidine Prepared from 2-(2-Aminoethyl)-5-(3-aminopropyl) thiophene and intermediate B analogous to example 10. Mass Spectrum (FAB) 267.3 ($MH^+$). $^1H$ NMR (200 MHz D2O) δ 6.75–6.7 (m, 2H), 3.50 (t, J=6.6 Hz, 2H), 3.23 (t, J=6.7 Hz, 2H), 3.07 (t, J=6.6 Hz, 2H), 2.85 (t, J=7.3 Hz, 2H), 2.14 (s, 6H), 2.0–1.9 (m, 2H).

EXAMPLE 19

Preparation of N-(3-(Aminomethyl)benzyl)-2,2-difluoroacetamidine

Prepared from tert-butyl N-(3-(aminomethyl)benzyl) carbamate and intermediate F analogous to example 1. $^1H$ NMR (200 MHz, D2O) δ 4.17 (2H, s), 4.64 (2H, s), 6.70 (1H, t, J=52.5 Hz), 7.47 (4H, m). Mass Spectrum (CI) 214.1 ($MH^+$, 100%).

EXAMPLE 20

Preparation ofN-(3-(Aminomethyl)benzyl)-2,2,2-trifluoroacetamidine

To an excess of freshly condensed trifluoroacetonitrile stirring at −78° C. was added a solution of tert-butyl N-[3-(aminomethyl) benzyl]carbamate (746 mg, 3.16 mmol) in $CH_3CN$ (5 ml) dropwise. The mixture froze into a solid white mass. After warming to room temperature, the mixture was warmed gently in a warm water bath to remove excess trifluoroacetonitrile. The mixture was concentrated at reduced pressure and the residue was chromatographed on silica gel eluting with 2:3 ethyl acetate in hexane to provide 897 mg (86%) of a viscous oil. To a stirred solution of the above oil (887 mg, 2.68 mmol) in dioxane (20 ml) was added 30% HBr in acetic acid (3 ml, 15.0 mmol). The resulting suspension was stirred for 6h, poured into ethyl acetate (200 ml) and stirred for 30 minutes. The solid was collected, suspended in hot iPrOH, cooled to rt. recollected and dried in vacuo to afford 731 mg (69%) of N-[3-(aminomethyl)benzyl]-2,2,2-trifluoroacetamidine as a dihydrobromide salt Mp=242°–244° C. 200 MHz $^1H$ NMR (D2O) δ 4.18 (2H, s), 4.67 (2H, s), 7.48 (4H, m).

EXAMPLE 21

Preparation of 3-(2-Fluoroacetimidoylamino) benzamide

A solution of 1.0 g (7.34 mmol) of 3-aminobenzamide in 15 ml of absolute ethanol at room temperature was treated with intermediate D and stirred 24 h. After concentration in vacuo to 5–10 ml, the residue was treated with $Et_2O$ and filtered to give 1.69 g of an off-white solid. Recrystallization from MeOH/Et2O provided 1.0 g (50%) of the title compound as a white solid: mp 219°–220° C.; $^1H$ NMR (D2O, 300 MHz) δ 7.70 (d, 1 H, J=7.6 Hz), 7.66 (s, 1 H), 7.56 (t, 1 H, J=7.6 Hz), 7.46 (d, 1 H, J=7.6 Hz), 5.46 (s, 1 H), 5.31 (s, 1 H).

The following compounds (22–43) were prepared in an analogous manner to example 21:

EXAMPLE 22

Preparation of 3-(Acetimidoylamino)benzamide

Prepared from 3-aminobenzamide (1.0 g) and intermediate B (1.63 g). The white solids were filtered and dried to yield 1.55 g of 3-(Acetimidoylamino)benzamide. Mass Spectrum (CI) 178.0 ($MH^+$, 100%).

EXAMPLE 23

Preparation of N-(3-(2-Hydroxyethyl)pheny) acetamidine

Prepared from 3-(2-hydroxyethyl)aniline and intermediate A. Mass Spectrum (CI) 179.0 ($MH^+$, 100%).

EXAMPLE 24

Preparation of N-(3-Fluorophenyl)acetamidine

Prepared from 3-fluoroaniline using intermediate A. Recrystallization from $MeOH/Et_2O$ provided 816 mg (48%) of the title compound as a white solid: mp 175°–177° C.; $^1H$ NMR (D2O, 200 MHz) δ 7.52 (m, 1 H), 7.28–7.05 (m, 3 H), 2.37 (s, 3 H).

EXAMPLE 25

Preparation of 3-(Acetimidoylamino)benzamidine

Prepared from 3-amino-benzamidino 2HCl using intermediate A and 1 equivalent of $Et_3N$. Recrystallization from $MeOH/Et_2O$ provided 1.48 g (82%) of a white solid: mp 263°–265° C.; $^1H$ NMR ($D_2O$, 300 MHz) δ 7.13 (dt, 1 H, J=7.8, 1.5 Hz), 7.66–7.52 (m, 3 H), 2.29 (s, 3H).

EXAMPLE 26

Preparation of N-(3-Nitrophenyl)acetamidine

Prepared from 3-nitroaniline using intermediate A. Recrystallization from $MeOH/Et_2O$ gave 513 mg (35%) of a white solid. The solid was dissolved in $CH_2Cl_2$, basified with saturated $NaHCO_3$, and extracted with $CH_2Cl_2$. The combined organic layers were dried ($Na_2SO_4$), filtered, and concentrated in vacuo. The yellow solid was treated with iPrOH followed by HCl in EtOH. $Et_2O$ was added, and resulting white solid was collected to give 310 mg of title compound: mp 226°–228° C.; $^1H$ NMR ($D_2O$, 300 MHz) δ 8.24–8.10 (m, 2 H), 7. 70–7.58 (m, 2 H), 2.31 (s, 3 H).

EXAMPLE 27

Preparation of N-(3-Acetylphenyl)acetamidine

Prepared from 3-aminoacetophenone using intermediate A. Recrystallization from $MeOH/Et_2O$ gave 1.16 g (74%) of a white solid. The solid was dissolved in $Et_2O$/saturated $NaHCO_3$, and the aqueous layer was extracted with $Et_2O$. The combined organics were dried ($Na_2SO_4$), filtered, and concentrated in vacuo. The residue was treated with $Et_2O$ and a small amount of HCl/ethanol. The resulting white solid was collected to give 325 mg of title compound: mp 204°–206° C.; IH NMR ($D_2O$, 300 MHz) δ 7.92 (dt, 1 H, J=7.6, 1.2 Hz), 7.77 (br s, 1 H), 7.55 (t, 1 H, J=7.6 Hz), 7.46 (dt, 1 H, J=7.6, 1.8 Hz), 2.52 (s, 3 H), 2.29 (s, 3 H).

EXAMPLE 28

Preparation of N-(3-Cyanophenyl)acetamidine

Prepared from 3-aminobenzonitrile using intermediate A. Recrystallization from $MeOH/Et_2O$ gave 814 mg (50%) of a solid. The solid was dissolved in $Et_2O$/saturated $NaHCO_3$, and the aqueous layer was extracted with $Et_2O$. The combined organics were dried ($Na_2SO_4$), filtered, and concentrated in vacuo. The residue was treated with $Et_2O$ and a small amount of HCl/ethanol. The resulting white solid was collected to give 576 mg of title compound: mp 228°–230° C.; $^1H$ NMR ($D_2O$, 300 MHz) δ 7.72 (dt, 1 H, J=7.8, 1.5 Hz), 7.64 (br s , 1 H), 7.62–7.49 (m, 2 H), 2.28 (s, 3 H).

EXAMPLE 29

Preparation of N-(3-Bromophenyl)acetamidine

Prepared from 3-bromoaniline using intermediate A. The resulting solid was dissolved in $Et_2O$/Saturated $NaHCO_3$, and the aqueous layer was extracted with $Et_2O$. The combined organics were dried ($Na_2SO_4$), filtered, and concentrated in vacuo. The residue was treated with $Et_2O$ and a small amount of HCl/ethanol. The resulting white solid was collected to give 776 mg (54%) of title compound: mp 208°–210° C.; $^1H$ NMR ($D_2O$, 300 MHz) δ 7.52 (d, 1 H, J=7.8 Hz), 7.43 (br s, 1 H), 7.31 (t, 1 H, J=7.8 Hz), 7.18 (d, 1 H, J=7.8 Hz), 2.26 (s, 3H).

EXAMPLE 30

Preparation of N-(3-(Methylthio)phenyl)acetamidine

Prepared from 3-(methylmercapto)-aniline using intermediate A. Recrystallization from MeOH/$Et_2O$ gave 1.11 g (71%) of a purple solid. The resulting solid was dissolved in $Et_2O$/saturated $NaHCO_3$, and the aqueous layer was extracted with $Et_2O$. The combined organics were dried ($Na_2SO_4$), filtered, and concentrated in vacuo. The residue was treated with $Et_2O$ and a small amount of HCl/ethanol. The resulting solid was collected to give 778 mg of title compound: mp 134°–135° C.; $^1H$ NMR ($D_2O$, 300 MHz) δ 7.33 (t, 1 H, J=7.8 Hz), 7.23 (d, 1 H, J=7.8 Hz), 7.09 (br s, 1 H), 6.97 (d, 1 H, J=7.8 Hz), 2.36 (s, 3H), 2.25 (s, 3H).

EXAMPLE 31

Preparation of N-(3-(1-Hydroxyethyl)phenyl) acetamidine

Prepared from (+)-3-(1-hydroxyethyl)aniline using intermediate C. Upon stirring overnight, the reaction was filtered, and the filtrate was concentrated in vacuo. The residue was triturated with absolute EtOH/pentane, and the title compound was collected by filtration to give 2.1 g (88%) of an off-white solid: mp 132°–135° C.; $^1H$ NMR ($D_2O$, 300 MHz) δ 7.40 (t, 1 H, J=7.8 Hz), 7.33 (d, 1 H, J=7.8 Hz), 7.19 (s, 1 H), 7.12 (d, 1 H, J=7.8 Hz), 4.80 (q, 1 H, J=6.6 Hz), 2.26 (s, 3 H), 1.32 (d, 3 H, J=6.6 Hz).

EXAMPLE 32

Preparation of N-(3-Acetimidoylamino)benzyl) acetamidine

A solution of 1.2 g (6.36 mmol) of 3-nitrobenzylamineoHCl in 50 ml of EtOH containing 150 mg of 10% palladium on carbon was placed on a Parr hydrogenator under $H_2$ for 1 h. The reaction was filtered through a pad of celite washing with EtOH, and the filtrate was concentrated in vacuo. The residue was dissolved in $CH_2Cl_2$ and treated with 1.0N NaOH. The aqueous layer was extracted with $CH_2Cl_2$, and the combined organic layers were dried ($MgSO_4$), filtered, and concentrated in vacuo to give 600 mg (77%) of 3-aminobenzyl amine which was used directly in the next reaction. The title compound was prepared as in example 21 from 600 mg of 3-aminobenzylamine using 2 equivalents of intermediate C. Recrystallization from MeOH/$Et_2O$ provided 1.46 g (81%) of a white solid: mp 276°–277° C.; $^1H$ NMR ($D_2O$, 300 MHz) δ 7.45 (t, 1 H, J=7.8 Hz), 7.31 (d, 1 H, J=7.8 Hz), 7.25–7.15 (m, 2 H), 4.41 (s, 2 H), 2.28 (s, 3 H), 2.15 (s, 3 H).

EXAMPLE 33

Preparation of N-(3-Acetimidoylamino) benzenesulfonamide

A solution of 1.5 g (7.42 mmol) of 3-nitrobenzenesulfonamide in 50 ml of EtOH containing 150 mg of 10% palladium on carbon was placed on a Parr hydrogenator under $H_2$ for 1 h. The reaction was filtered through a pad of celite washing with EtOH, and the filtrate was concentrated in vacuo to give 1.28 g (100%) of 3-aminobenzenesulfonamide which was used immediately in the next reaction. The tide compound was prepared as in example 21 from 3-aminobenzenesulfonamide using intermediate C. Recrystallization from MeOH/$Et_2O$ provided 1.46 g (67%) of title compound as an off-white solid: mp 240°–242° C.; $^1H$ NMR (D2O, 300 MHz) δ 7.86 (d, 1 H, J=8.1 Hz), 7.75 (s, 1 H), 7.63 (t, 1 H, J=8.1 Hz), 7.51 (d, 1 H, J=8.1 Hz), 2.30 (s, 3 H).

EXAMPLE 34

Preparation of N-(3-((1,2,3,4-Tetrahydroisoquinol-2-yl) methyl)phenyl)acetamidine A solution of 1.0 g (4.63 mmol) of 3-nitrobenzyl bromide in 30 ml of toluene was treated with 1.16 ml (9.26 mmol, 2 equiv) of 1,2,3,4-tetrahydroisoquinoline. After heating at reflux for 1 h followed by cooling to 25° C., the reaction was diluted with EtOAc, washed with 1N NaOH, dried ($MgSO_4$), filtered, and concentrated in vacuo. The residue was filtered through a pad of silica gel eluting with hexanes/$Et_2O$ (2:1), and the filtrate was concentrated in vacuo to give 1.21 g (76%) of intermediate. A solution of 1.21 g (3.50 mmol) of the above nitroaromatic in 50 ml of EtOAc was treated with 140 mg of 10% palladium on carbon and placed on a Parr hydrogenator under $H_2$ until gas consumption ceased. The reaction was filtered through a pad of silica gel washing with EtOAc, and the filtrate was concentrated in vacuo to give 1.0 g (89%) of a yellow solid that was used immediately in the next reaction. The title compound was prepared from 1.0 g (3.13 mmol) of the above compound as in example 21 using intermediate C. After removal of EtOH, 10 ml of 1,4-dioxane was added followed by 1.2 ml of 3.7M HBr in AcOH. After stirring for 5 min, the reaction was treated with $Et_2O$ and stirred 3 h. An orange solid was collected and recrystallized from EtOH/EtOAc to give 366 mg (27%) of title compound as a brown solid: mp 260°–262° C.; $^1H$ NMR ($D_2O$, 300 MHz) δ 7.64–6.94 (m, 8 H), 4.41 (br s, 2 H), 4.26 (s, 2 H), 3.69 (br s, 1 H), 3.36 (br s, 1 H), 3.06 (br s, 1 H), 2.29 (s, 3 H).

EXAMPLE 35

Preparation of N-(3-(2-Amino-4-thiazolyl)phenyl) acetamidine

To a solution of 5 g (20.5 mmol) of a-bromo-3-nitroacetophenone in 20 ml of acetone at 25° C. was treated with 1.6 g (20.5 mmol, 1 equiv) of thiourea. After stirring overnight, 6.1 g (98%) of a white solid was collected by filtration. A solution of 5.1 g (16.9 mmol) of the above compound in 200 ml of EtOH was treated with 500 mg of 10% palladium on carbon and placed on a Parr hydrogenator under $H_2$ for 2.5 h. The reaction was filtered through a pad of celite washing with EtOH, and the filtrate was concentrated in vacuo. The residue was dissolved in $CH_2Cl_2$ and basified with 1N NaOH. The aqueous layer was extracted with $CH_2Cl_2$, and the combined organic layers were dried ($MgSO_4$), filtered, and concentrated in vacuo to give 1.78 g (55%) of intermediate which was used directly in the next reaction. The title compound was prepared as in example 21 from 1.03 g (5.38 mmol) of the above compound using intermediate C. After removal of EtOH, the residue was diluted with 10 ml of 1,4-dioxane and acidified with 3.7M HBr in AcOH. After stirring 30 min, $Et_2O$ was added and a solid was collected by filtration. The solid was recrystallized from MeOH/$Et_2O$ to give 1.09 g (51%) of title compound as a white solid: mp 252°–254° C.; $^1$H NMR ($D_2O$, 300 MHz) δ 7.62–7.40 (m, 3 H), 7.29 (br d, 1 H, J=7.5 Hz), 6.91 (s, 1 H), 2.29 (s, 3 H).

EXAMPLE 36

Preparation of N-(3-Aminophenyl)acetamidine

A solution of 10 g (72.4 mmol) of 3-nitroaniline in 200 ml of $CH_2Cl_2$ at 25° C. was treated sequentially with 10 ml (71.4 mmol) of $Et_3N$, 17.4 g (72.4 mmol) of $BOC_2O$, and a catalytic amount of DMAP. After stirring for 72 h, the reaction was filtered through a pad of silica gel washing with hexanes/EtOAc (1:1), and the filtrate was concentrated in vacuo. Purification by medium pressure silica gel column chromatrography using hexanes/EtOAc (3:1→1:1) provided 4.4 g (26%) of 3-(N-tert-butoxycarbonyl)-nitroaniline which was used directly in the next reaction. A solution of 1.5 g (6.3 mmol) of the nitroaromatic in 50 ml of EtOAc was treated with 150 mg of 10% palladium on carbon and placed on a Parr hydrogenator under $H_2$ for 2 h. The reaction was filtered through a pad of silica gel washing with EtOAc, and the filtrate was concentrated in vacuo to give 1.3 g (100%) of intermediate which was used directly in the next reaction. The title compound was prepared as in example 21 from 1.3 g (6.3 mmol) of 3-(N-tert-butoxycarbonyl)-aminoaniline using intermediate C. After removal of EtOH, the residue was diluted with 10 ml of 1,4-dioxane and treated with 2 ml (7.6 mmol, 1.2 equiv) of 3.7M HBr in AcOH. After string 15 min, $Et_2O$ was added and a solid was collected by filtration. The solid was recrystallized from MeOH/EtOAc to give 1.15 g (59%) of title compound as a white solid: mp 288°–289° C.; $^1$H NMR ($D_2O$, 300 MHz) δ 7.51 (t, 1 H, J=8.1 Hz), 7.33–7.24 (m, 2 H), 7.20 (t, 1 H, J=1.8 Hz), 2.27 (s, 3H).

EXAMPLE 37

Preparation of N-(3-((Methylamino)methyl)phenyl) acetamidine

To a solution of 2.0 g (7.93 mmol) of 3-(N-tert-butoxycarbonyl)-nitrobenzylamine in 32 ml of anhydrous THF at −78° C. was added 6.34 ml (9.51 mmol, 1.2 equiv) of 1.5M LDA in cyclcohexane. After stirring for 25 min, 0.592 ml (9.51 mmol, 1.2 equiv) of MeI was added, and the reaction was immediately warmed to 25° C. and stirred 4 h. The solution was poured into $H_2O$ and extracted with $Et_2O$. The combined organic layers were dried ($MgSO_4$), filtered, and concentrated in vacuo. Purification by flash silica gel column chromatography using hexanes/$Et_2O$ (2:1) provided 2.1 g (59%) of intermediate 3-(N-methyl-N-tert-butoxycarbonyl) nitrobenzylamine. A solution of 1.25 g (4.7 mmol) of the above nitroaromatic in 50 ml of EtOAc at 25° C. was treated with 140 mg of 10% palladium on carbon and placed on a Parr hydrogenator under $H_2$ for 4 h. The reaction was filtered through a pad of silica gel washing with EtOAc. The filtrate was concentrated in vacuo to give 1.11 g (100%) of intermediate. The title compound was prepared analogous to example 21 from the above aniline intermediate (1.11 g ,4.69 mmol) and intermediate C. After removal of EtOH, 10 ml of 1,4-dioxane was added followed by 1 ml (5.9 mmol) of 5.9M HBr/AcOH. After stirring 5 min, Et2O was added and stirring was continued for 2 h. Filtration provided a solid that was recrystallized from MeOH/EtOAc to give 950 mg (59%) of title compound as a white solid: mp 222°–223° C.; $^1$H NMR ($D_2O$, 300 MHz) δ 7.54–7.24 (m, 4 H), 4.12 (s, 2 H), 2.60 (s, 3 H), 2.28 (s, 3 H).

EXAMPLE 38

Preparation of N,N'-(1,3-Phenylene)diacetamidine

Prepared from 1,3-phenylene-diamine using 2 equivalents of intermediate C. Recrystallization from MeOH/$Et_2O$ provided 1.55 g (53%) of title compound as a white solid: mp 256°–258° C.; $^1$H NMR ($D_2O$, 300 MHz) δ 7.56 (t, 1 H. J=8.1 Hz), 7.36–7.20 (m, 3 H), 2.28 (s, 6 H).

EXAMPLE 39

Preparation of N-(3-Hydroxyphenyl)acetamidine

Prepared from 3-aminophenol using intermediate C. Trituration with MeOH/$Et_2O$ provided 1.9 g (90%) of title compound as a white solid: mp 115°–118° C.; $^1$H NMR ($D_2O$, 300 MHz) δ 7.26 (t, 1 H, J=8.1 Hz), 6.81 (d, 1 H, 8.1 Hz), 6.73 (d, 1 H, J=8.1 Hz), 6.66 (br s, 1 H), 2.23 (s, 3 H).

EXAMPLE 40

Preparation of N-(3-(Hydrazinomethyl)phenyl) acetamidine

A solution of 1.0 g (5.3 mmol) of 3-nitrophenylhydrazineoHCl in 66 ml of THF was treated with 33 ml of saturated $NaHCO_3$ followed by 1.15 g (5.3 mmol, 1 equiv) of $BOC_2O$. After stirring overnight, the reaction was diluted with $H_2O$ and extracted with $Et_2O$. The combined organic layers were washed with brine, dried ($MgSO_4$), filtered, and concentrated in vacuo to give 1.33 g (100%) of a yellow solid that was used immediately in the next reaction. A solution of 1.33 g (5.3 mmol) of the crude intermediate in 50 ml of EtOAc at 25° C. was treated with 200 mg of 10% palladium on carbon and placed on a Parr hydrogenator under $H_2$ until gas consumption ceased. The reaction was filtered through a pad of celite washing with EtOAc, and the filtrate was concentrated in vacuo to give 1.18 g (100%) of a yellow solid that was used immediately in the next reaction. The title compound was prepared as in example 21 using the above intermediate aniline and intermediate C. After removal of EtOH, 10 ml of 1,4-dioxane was added followed by 1 ml of 5.9M HBr in AcOH. After stirring for 30 min $Et_2O$ was added, and a solid was collected by filtration. The solid was recrystallized from MeOH/EtOAc to give 0.78 g (45%) of title compound as a brown solid: mp 218°–220° C.; $^1$H NMR ($D_2O$, 300 MHz) δ 7.38 (t, 1 H, J=8.1 Hz), 6.96–6.88 (m, 2 H), 6.81 (t, 1 H, J=2.1 Hz), 2.26 (s, 3 H).

EXAMPLE 41

Preparation of N-(4-(Aminomethyl)phenyl) acetamidine

A solution of 1. 15 g (6.1 mmol) of 4-nitrobenzylamineoHCl in 76 ml of THF was treated with 38 mL of saturated $NaHCO_3$ followed by 1.33 g (6.1 mmol, 1 equiv) of $BOC_2O$. After stirring overnight the reaction was diluted with $H_2O$ and extracted with Et2O. The combined organic layers were dried ($MgSO_4$), filtered, and concentrated in vacuo to give 1.54 g (100%) of 4-(N-tert-butoxycarbonyl)-nitrobenzylamine that was used immediately in the next reaction.

A solution of 1.54 g (6.1 mmol) of the above compound in 50 ml of EtOAc was treated with 150 mg of 10% palladium on carbon and placed on a Parr hydrogenator under $H_2$ under gas consumption ceased. The reaction was filtered through a pad of celite washing with EtOAc, and the filtrate was concentrated in vacuo to give 1.36 g (100%) of intermediate aniline. The title compound was prepared from 1.36 g (6.1 mmol) of the above aniline as in example 21 using intermediate C. After EtOH removal, 10 ml of 1,4-dioxane was added followed by 1.2 ml of 5.9M HBr in AcOH. After stirring for 5 min $Et_2O$ was added, and a solid was collected by filtration. The solid was recrystallized from MeOH/EtOAc to give 1.2 g (61%) of title compound as a white solid: mp 256°–258° C.; $^1H$ NMR ($D_2O$, 300 MHz) δ 7.47 and 7.28 (AB quartet, 2 H, J=8.4 Hz), 4.10 (s, 2 H), 2.28 (s, 3 H).

EXAMPLE 42

Preparation of N-(1,2,3,4-Tetrahydroisoquinolin-7-yl)acetamidine

A solution of 10.5 g (78.8 mmol) of 1,2,3,4-tetrahydroisoquinoline in 55 ml of concentrated $H_2SO_4$ at 0° C. was treated with 10 g (98.9 mmol, 1.25 equiv) and warmed to 25° C. After stirring for 48 h, ice was added followed by $NH_4OH$. The aqueous layer was extracted with $CH_2Cl_2$, and the combined organics were dried ($MgSO_4$), filtered, and concentrated to a volume of 100 ml. The solution was treated with 80 ml of 1M HCl in $Et_2O$ followed by $Et_2O$. A solid was collected and recrystallized from $H_2O$/acetone to give 6.0 g (36%) of 7-nitro-1,2,3,4-tetrahydroisoquinolineoHCl. A solution of 1.0 g (4.7 mmol) of 7-nitro-1,2,3,4-tetrahydroisoquinolineoHCl in 58 ml of THF was treated with 29 ml of saturated $NaHCO_3$ followed by 1.02 g (4.7 mmol, 1 equiv) of $BOC_2O$. After stirring overnight the reaction was diluted with $H_2O$ and extracted with $Et_2O$. The combined organic layers were dried ($MgSO_4$), filtered, and concentrated in vacuo. Pufication by flash silica gel column chromatography eluting with hexanes/$Et_2O$ (2:1) provided 1.08 g (83%) of N-tert-butoxycarbonyl-7-nitro-1,2,3,4-tetra hydroisoquinoline. A solution of 1.08 g (3.88 mmol) of the above nitroaromatic in 50 ml of EtOAc was treated with 100 mg of 10% palladium on carbon and placed on a Parr hydrogenator under $H_2$ until gas consumption ceased. The reaction was filtered through a pad of silica gel washing with EtOAc, and the filtrate was concentrated in vacuo to give 964 mg of an intermediate aniline that was used immediately in the next reaction. The title compound was prepared as in example 21 using 0.964 g (3.88 mmol) of the above aniline and intermediate C. After EtOH removal, 10 ml of 1,4-dioxane was added followed by 0.75 ml of 5.9M HBr in AcOH. After stirring 5 min $Et_2O$ was added, and a solid was collected. Recrystallization from MeoH/EtOAc provided 530 mg (39%) of title compound as a white solid: mp undefined; $^1H$ NMR ($D_2O$, 300 MHz) δ 7.29 (d, 1 H, J=8.4 Hz), 7.12 (d, 1 H, J=8.4 Hz), 7.06 (br s, 1 H), 4.27 (s, 2 H), 3.41 (t, 2 H, J=6.6 Hz), 3.02 (t, 2 H, J=6.6 Hz), 2.26 (s, 3 H).

EXAMPLE 43

Preparation of N-(1H-Indazol-6-yl)acetamidine

The title compound was prepared from 6-aminoindazole as in example 21 using intermediate C. Recrystallization from MeOH/EtOAc provided 900 mg (70%) of title compound as a brown solid: mp 244°–246° C.; $^1H$ NMR (DMSO, 300 MHz) δ 13.30 (s, 1 H), 11.23 (s, 1 H), 9.41 (s, 1 H), 8.53 (s, 1 H), 8.14 (s, 1 H), 7.90 (d, 1 H, J=8.4 Hz), 7.50 (s, 1 H), 6.98 (d, 1 H, J=8.4 Hz), 2.34 (s, 3 H).

EXAMPLE 44

Preparation of N,N'-(3,3'-(Iminodimethylene) diphenyl)diacetamidine

A solution of 1.0 g (4.63 mmol) of 3-nitrobenzyl bromide in 20 ml of DMPU was treated with 873 mg (4.63 mmol, 1 equiv) of 3-nitrobenzylamineoHCl followed by 1.5 g (13.9 mmol, 3 equiv) of $Na_2CO_3$. After stirring at 100° C. for 1 h, the reaction was cooled to 25° C. and treated with 1.06 g (4.63 mmol, 1 equiv) of $BOC_2O$. After stirring for 48 h, the reaction was poured into H2O and extracted with hexanes/EtOAc (1:1). The combined organic layers were dried ($MgSO_4$), filtered, and concentrated in vacuo. Purifcation by flash silica gel column chromatrography eluting with hexanes/$Et_2O$ (1:1) provided 1.26 g (70%) of bis-nitroaromatic intermediate. A solution of 1.26 g (3.25 mmol) of the above compound in 50 ml of EtOAc was treated with 150 mg of 10% palladium on carbon and placed on a Parr hydrogenator under $H_2$ until gas consumption ceased. The reaction was filtered through a pad of celite washing with EtOAc, and the filtrate was concentrated in vacuo to give 1.07 g (100%) of an oil that was used directly in the next reaction. The title compound was prepared from 1.06 g (3.25 mmol) of the above diamine as in Example 21 using 2 equivalents of intermediate C. After EtOH removal, 10 ml of 1,4-dioxane was added followed by 0.75 ml of 5.9M HBr in AcOH. After stirring for 5 min $Et_2O$ was added and stirring was continued for 2 h. A solid was collected and recrystallized from MeOH to give 708 mg (40%) of title compound as a white solid: mp 282°–283° C.; $^1H$ NMR ($D_2O$, 300 MHz) δ 7.54–7.25 (m, 8 H), 4.23 (s, 4 H), 2.28 (s, 6 H).The following compound (45) was prepared in an analogous fashion:

EXAMPLE 45

Preparation of N-(3-((Hydroxyamino)methyl) phenyl)acetamidine

The title compound was prepared from 482 mg (6.94 mmol) of hydroxylamine and intermediate C for the amidine formation. Recrystallization from MeOH/EtOAc provided 600 mg (47%) of tide compound as a white solid: mp 214°–215° C.; $^1H$ NMR ($D_2O$, 300 MHz) δ 7.5–7.25 (m, 2 H), 7.36–7.28 (m, 2 H), 4.35 (s, 2 H), 2.28 (s, 3 H).

EXAMPLE 46

Preparation of N-(3-(1H-Pyrazol-3-yl)phenyl) acetamidine

A solution of 5.0 g (30.3 mmol) of 3-nitroacetophenone in 16 ml of DMF was treated with 4.8 mL of $(MeO)_2CHNMe_2$ and heated to 120° C. for 24 h. After cooling to 25° C., the reaction poured into 1N HCl and extracted with hexanes/EtOAc (1:1). The combined organic layers were washed with brine, dried ($MgSO_4$), filtered, and concentrated in vacuo to give 1.88 g (28%) of intermediate.

A solution of 940 mg (4.27 mmol) of the above compound in 34 ml of MeOH and 8.5 ml of $H_2O$ was treated with 0.855 ml (17.6 mmol) of $H_2NNH_2oH_2O$ and heated at reflux for 2 h. After cooling to 25° C., the reaction was poured into 1N HCl and extracted with EtOAc. The combined organic layers were dried ($MgSO_4$), filtered, and concentrated in vacuo to give 808 mg (100%) of 1-(1H-pyrazol-3-yl)-3-nitrobenzene.

A solution of 808 mg (4.27 mmol) of the above intermediate in 21 ml of $CH_2Cl_2$ was treated with a catalytic amount of DMAP followed by 918 mg (4.27 mmol, 1 equiv) of $BOC_2O$. After stirring overnight, the reaction was concentrated in vacuo and used immediately in the next reaction.

A solution of 1.23 g (4.27 mmol) of the above intermediate in 50 ml of EtOAc was treated with 150 mg of 10% palladium on carbon and placed on a Parr hydrogenator under $H_2$ atmosphere until gas consumption ceased. The reaction was filtered through a pad of celite washing with EtOAc, and the filtrate was concentrated in vacuo to give an oil that was used immediately in the next reaction.

The title compound was prepared from 1.1 g (4.27 mmol) of the above intermediate as in Example 21 using intermediate C. After EtOH removal, 10 ml of 1,4-dioxane was added followed by 0.80 ml of 5.9M HBr in AcOH. After stirring for 30 min $Et_2O$ was added, and stirring was continued for 2 h. A solid was collected and recrystallized from EtOH/EtOAc/$Et_2O$ to give 381 mg (25%) of title compound as a brown solid: mp 224°–226° C.; $^1$H NMR ($D_2O$, 300 MHz) δ 7.81 (d, 1 H, J=2.4 Hz), 7.67 (dd, 1 H, J=8.1, 1.2 Hz), 7.55 (br s, 1 H), 7.49 (t, 1 H, J=8.1 Hz), 7.25 (br d, 1 H, J=8.1 Hz), 6.75 (d, 1 H, J=2.4 Hz), 2.28 (s, 3 H).

EXAMPLE 47

Preparation of N-(3-(Morpholinomethyl)phenyl) acetamidine2HBr

A solution of 1.0 g (4.63 mmol) of 3-nitrobenzyl bromide in 30 ml of toluene was treated with 0.806 ml (9.26 mmol, 2 equiv) of morpholine and heated to reflux for 3 h. After cooling to 25° C. EtOAc was added, and the organic layer was washed with 1N NaOH, dried ($MgSO_4$), filtered, and concentrated in vacuo to give 1.03 g (100%) of an oil.

The crude oil from above was dissolved in 50 ml of EtOAc, treated with 100 mg of palladium on carbon, and placed on a Parr hydrogenator under $H_2$ for 1.5 h. The mixture was filtered through a pad of silica gel washing with EtOAc/MeOH (10:1), and the filtrate was concentrated in vacuo to give 900 mg of an oil.

The title compound was prepared as in Example 21 from 890 mg (4.63 mmol) of the above oil using intermediate C. After EtOH removal, 10 ml of 1,4-dioxane was added followed by 0.90 ml of 5.9M HBr in AcOH. After stirring for 5 min $Et_2O$ was added, and a solid was collected. Recrystallization from EtOH/EtOAc provided 938 mg (51%) of title compound as a white solid: mp 219°–220° C.; $^1$H NMR ($D_2O$, 300 MHz) δ 7.56–7.28 (m, 4 H), 4.28 (s, 2 H), 3.93 (br s, 2H), 3.63 (br s, 2 H), 3.40–3.00 (m, 4 H), 2.28 (s, 3 H).

The following compounds (48–50) were made in an analogous fashion:

EXAMPLE 48

Preparation of N-(3-(1H Pyrazol-1-ylmethyl) phenyl)acetamidineo2 HBr

The title compound was prepared from pyrazole as in Example 47 utilizing intermediate C for the amidine formation. Recrystallization from MeOH/EtOAc provided 960 mg (55%) of a white solid: 218°–220° C.; $^1$H NMR ($D_2O$, 300 MHz) δ 7.79 (s, 1 H), 7.63 (s, 1 H), 7.40 (t, 1 H, J=7.8 Hz), 7.24–7.13 (m, 2 H), 7.03 (s, 1 H), 6.38 (m, 1 H), 5.35 (s, 2 H), 2.23 (s, 3 H).

EXAMPLE 49

Preparation of N-(3-((Dimethylamino)methyl) phenyl) acetamidineo2HBr

The title compound was prepared from 2M $HNMe_2$ in THF as in Example 47 utilizing intermediate C for the amidine formation. Recrystallization from MeOH/EtOAc provided 960 mg (56%) of a white solid: mp 242°–243° C.; $^1$H NMR ($D_2O$, 300 MHz) δ 7.58–7.28 (m, 4 H), 4.23 (s, 2 H), 2.73 (s, 6 H), 2.28 (s, 3 H); low resolution MS (CI) 192 (MH+); Anal. Calcd. for $C_{11}H_{17}N_3$o2HBr: C, 37.42; H, 5.42; N, 11.90; Br, 45.26. Found: C, 37.45; H, 5.46; N, 11.81; Br, 45.16.

EXAMPLE 50

Preparation of N-(3-((2-pyridyiamino)methyl) phenyl)acetamidineo2HBr

A solution of 1.0 g (4.63 mmol) of 3-nitrobenzyl bromide in 30 ml of toluene was treated with 872 mg (9.26 mmol, 2 equiv) of 2-aminopyridine and heated to reflux for 4 h. Upon cooling to 25° C. the reaction mixture was basified with 1N NaOH and extracted with EtOAc. The combined organic layers were dried ($MgSO_4$), filtered, and concentrated in vacuo to an oil that was used in the next reaction.

A solution of 1.06 g (4.63 mmol) of the above amine in 30 ml of THF was treated with 1.5 g (6.95 mmol, 1.5 equiv) of $BOC_2O$ and stirred 16 h. The reaction was treated with 1.5 g (6.95 mmol, 1.5 equiv) of $BOC_2O$ and stirred an additional 7.5 h. The reaction was diluted with saturated $NaHCO_3$ and extracted with $Et_2O$. The combined organic layers were dried ($MgSO_4$), filtered, and concentrated in vacuo. Purification by flash silica gel column chromatrography eluting with hexanes/EtOAc (3:1) provided 411 mg (27%) of an oil that was used in the next reaction.

A solution of 411 mg (1.25 mmol) of the above nitroaromatic in 20 ml of EtOAc was treated with 100 mg of 10% palladium on carbon and placed on a Parr hydrogenator under $H_2$ for 3 h. The reaction was filtered through celite washing with EtOAc, and the filtrate was concentrated in vacuo to give 374 mg (100%) of an oil.

The title compound was prepared from 374 mg (1.25 mmol) of the above oil as in example 47 using intermediate C. After removal of EtOH, 5 ml of 1,4-dioxane was added following by 0.30 ml of 5.9M HBr in AcOH. After stirring for 5 min $Et_2O$ was added, and stirring was continued overnight. A solid was collected and recrystallized from MeOH/EtOAC to give 270 mg (54%) of title compound as a white solid: mp 247°–248° C.; $^1$H NMR ($D_2O$, 300 MHz) δ 7.76 (ddd, 1 H, J=9.2, 7.2, 1.8 Hz), 7.65 (d, 1 H, J=6.3 Hz), 7.41 (t, 1 H, J=7.6 Hz), 7.33 (d, 1 H, J=7.6 Hz), 7.22–7.13 (m, 2 H), 6.88 (d, 1 H, J=9.2 Hz), 6.77 (t, 1 H, J=6.3 Hz), 4.53 (s, 2 H), 2.25 (s, 3 H).

EXAMPLE 51

Preparation of S-(3-(Acetimidoylamino)benzyl) isothioureao2HBr

A solution of 1.0 g (4.63 mmol) of 3-nitrobenzyl bromide in 10 ml of acetone was treated with 352 mg (4.63 mmol, 1 equiv) of thiourea and stared for 3 h. The reaction was filtered to give 1.29 g (96%) of a white solid that was used directly in the next reaction.

A solution of 1.29 g (4.41 mmol) of the above compound in 50 ml of EtOH was treated with 200 mg of 10% palladium on carbon and placed on a Parr hydrogenator under $H_2$ atmosphere overnight. The reaction mixture was filtered through a pad of celite washing with EtOH, and the filtrate was concentrated in vacuo to give 1.26 g (100%) of an orange solid that was used immediately in the next reaction.

The title compound was prepared from 1.16 g (4.41 mmol) of the above intermediate as in Example 21 using intermediate C. Recrystallization from MeOH/EtOAc provided 672 mg (40%) of title compound as a brown solid: mp 228°–230° C.; $^1$H NMR ($D_2O$, 300 MHz) δ 7.46–7.12 (m, 4 H), 4.31 (s, 2 H), 2.27 (s, 3 H).

EXAMPLE 52

Preparation of N-(3(Aminomethyl)phenyl)-2-fluoroacetamidine

Preparation of intermediate Tert-butyl N-(3-nitro) benzylcarbamate

To a 0° C. solution of 30 g (0.159 mol) of 3-nitrobenzylamine hyydrochloride in MeOH (100 ml), THF (100 ml) and 48.8 ml triethylamine was added a solution of 38.2 g (0.175 mol) di-tert-butyl dicarbonate in THF (200 ml) over 60 min. After 1 hr, the solution was concentrated, diluted with 100 ml water, and extracted with EtOAc (2×100 ml). The dried ($Na_2SO_4$) solution was concentrated and purified by silica gel chromatography eluting with 10%–30% EtOAc in hexanes to yield 38 g (95%) of tert-butyl N-(3-nitro)benzylcarbamate.

Amidine synthesis:

A solution of 10 g (39.64 mmol) of tert-butyl N-(3-nitro) benzyl -carbamate in 100 ml EtOAc was hydrogenated. under 55 psi $H_2$ in the presence of 1 g of 10% Pd on carbon for 90 min. The residue after filtration and concentration was taken into 100 ml of absolute ethanol at 0° C. and 16 g (50.8 mmol) of intermediate E was added. The solution was stirred for 16 h and concentrated to a volume of 15 ml before 500 ml of ether was added with rapid stirring. The resulting residue was taken into 75 ml of acetic acid and 15 ml of 30% HBr in acetic acid solution was added. After 15 min 500 ml of ether was added, the mixture stirred for 30 min, and the pale yellow solids collected via filtration to yield 13.5 g (99%). Recrystallization of 7 g from 30 ml MeOH and 150 mL EtOAC gave 6.0 g of white solid N-(3-(Aminomethyl) phenyl)-2-fluoroacetamidine. Mass Spectrum (CI)182 ($MH^+$, 9.7%). $^1$H NMR (300 MHz, DMSO) δ 7.61–7.32 (m, 4H), 5.5 (d, J=45.1 Hz, 2H), 4.08 (s, 2H).

EXAMPLE 53

Preparation of N-(3-(2-Aminoethyl)phenyl) acetamidine

3-Nitrophenethyl alcohol (2.5 g) was hydrogenated (55 psi, 20° C.) in MeOH (100 ml) in the presence of di-tert-butyl dicarbonate (3.6 g) and 750 mg of 10% palladium on carbon to give 3.7 g (100%) of BOC-protected intermediate (mass spec. 238.0, $MH^+$). 3.55 g of this alcohol intermediate was converted to azide via the bromide($CBr_4$, $PPh_3$, $CH_2Cl_2$, then $NaN_3$ in DMF) to provide 1.65 g. Reduction of the azide (1.16 g, EtOAc, Pd/C, 20° C., 55 psi $H_2$) followed by protection ($K_2CO_3$, $CH_2Cl_2$, $H_2O$, CBz-Cl) gave 1.6 g (100%) of intermediate. The BOC protecting group was removed at 0° C. in $CH_2Cl_2$ with TFA. The crude material was free based with $NaHCO_3$ and the resulting residue (with intermediate A) was converted to the intermediate N-(3-(2-(Benzyloxycarbonyl) aminoethyl)phenyl) acetamidine (1.5 g) analogous to example 1. A MeOH (75 ml) and 3.0M HCl in EtOH (25 ml) solution of this acetamidine (1.2 g) was hydrogenated at 55 psi $H_2$ at 20° C. for 4 h. Filtration through celite and concentration gave the title compound. Mass Spectrum (CI)178.2 ($MH^+$, 100%). $^1$H NMR (300 MHz, $D_2O$) δ 7.4–7.1 (m, 4H), 3.14 (t, J=7.1 Hz, 2H), 2.89 (t, J=7.1 Hz, 2H), 2.25 (s, 3H).

EXAMPLE 54

Preparation of N-(3-(Aminomethyl)benzyl) propionamidine

Prepared from tert-butyl N-(3-(aminomethyl)benzyl carbamate (1.0 g) and intermediate J as in example 2 to yield 1.25 g of white solid. A 1.0 g portion of this solid was recrystallized from MeOH/EtOAc to yield 0.93 g of the title compound. $^1$H NMR (200 MHz, $D_2O$) δ 7.5–7.38 (m, 4H), 4.52 (s, 2H), 4.18 (s, 2H), 2.53 (q, J=7.7 Hz, 2H), 1.25 (t, J=7.7 Hz, 3H).

EXAMPLE 55

Preparation of 2-Amino-N-(3-Aminomethyl)phenyl) acetamidine

Prepared from tert-butyl N-(3-(aminomethyl)benzyl) carbamate and intermediate I analogous to example 2. $^1$H NMR (200 MHz, $D_2O$) δ 4.25 (4H, d, J=5.5 Hz), 7.78–7.40 (4H, m). Mass Spectrum (CI) 179.1 (MH+, 100%).

EXAMPLE 56

Preparation of N-(3-Aminomethyl)phenyl)-2-(methylthio)acetamidine

Prepared from tert-butyl N-(3-(aminomethyl)benzyl) carbamate and intermediate H analogous to example 1. $^1$H NMR (200 MHz, DMSO) δ 2.30 (3H, s), 3.64 (2H, s), 4.12 (2H, s), 7.65–7.32 (4H, m). Mass Spectrum (CI) 210.0 (MH+, 60.5%).

EXAMPLE 57

Preparation of N-(1,2,3,4-tetrahydro-7-isoquinolyl) methyl)acetamidineo2HBr

To a solution of 5.0 g (37.5 mmol) of 1,2,3,4,-tetrahydroisoquinoline in 23 ml of concentrated $H_2SO_4$ at 25° C. was treated with 6.7 g (37.5 mmol, 1 equiv) of N-hydroxymethylphthalimide and stirred for 7 days. The reaction was poured into $H_2O$, basified with solid $NaHCO_3$, and extracted with $Et_2O$. The combined organics were dried ($MgSO_4$), filtered, and concentrated in vacuo. The residue was dissolved in $Et_2O$ and acidified with 1M HCl in $Et_2O$. The solid was collected and recrystallized from MeOH/$Et_2O$ to give 1.7 g (10%) of intermediate that was used in the next reaction.

A solution of 500 mg (1.52 mmol) of the above compound in 19 ml of THF was treated with 9 ml of saturated $NaHCO_3$ followed by 332 mg (1.52 mmol, 1 equiv) of BOC2O. After stirring for 48 h, the reaction was diluted with $H_2O$ and extracted with $Et_2O$. The combined organic layers were dried ($MgSO_4$), filtered, and concentrated in vacuo. Purification by flash silica gel column chromatography eluting with hexanes/$Et_2O$ (1:1) provided 474 mg (79%) of N-protected tetrahydroisoquinoline.

A solution of 474 mg (1.21 mmol) of the above compound in 12 ml of EtOH was treated with 0.117 ml (2.41 mmol, 2 equiv) of $H_2NNH_2oH_2O$ and stirred for 36 h. The reaction was diluted with $CH_2Cl_2$ and filtered. After concentration in vacuo, the residue was dissolved in $CH_2Cl_2$ and filtered. The filtrate was concentrated in vacuo and used in the next reaction.

The title compound was prepared from the above intermediate as in example 21 using intermediate C. After EtOH removal, 2 ml of 1,4-dioxane was added followed by 0.50 ml of 5.9M HBr in AcOH. After stirring for 15 min $Et_2O$ was added, and the supernatant was decanted. The residue was triturated with isopropanol overnight. Filtration provided 272 mg (62%) of title compound as an off-white solid: mp 215°–218° C.; $^1H$ NMR ($D_2O$, 300 MHz) δ 7.12–6.88 (m, 3 H), 4.21 (s, 2 H), 4.12 (s, 2 H), 3.27 (t, 1 H, J=6.3 Hz), 2.87 (t, 1 H, J=6.3 Hz), 2.01 (s, 3 H).

EXAMPLE 58

Preparation of 2-Fluoro-N-(3-(2-hydroxymethyl) phenyl)acetamidine

The title compound (2.19 g) was prepared as a pale yellow solid from 3-aminophenethyl alcohol (1.0 g) and intermediate D (2.32 g) as in example 1. $^1H$ NMR (300 MHz, $D_2O$) δ 7.5 (t, J=7.5 Hz, 1H), 7.37 (d, J=7.8 Hz, 1H), 7.2 (m, 2H), 5.4 (d, J=44.9 Hz, 2H), 3.83 (t, J=6.4 Hz), 2.87 (t, J=6.4 Hz, 2H). Mass Spectrum (CI) 197.0 (MH+, 100%)

EXAMPLE 59

Preparation of N-(3-Amino-5-indanyl)acetamidine

6-Nitroindan-1-one (18.1 g, 102 mmol) was dissolved in ethanol (400 ml) and reduced using Pd (5%) on carbon (2.0 g) and 35 psi hydrogen pressure on a Parr apparatus. Filtration on celite followed by evaporation gave 6-aminoindan-1-one (13.7 g, 93 mmol). NMR (DMSO) 7.2 (d, J=7.7Hz, 1H), 6.9 (dd, Jab=7.7Hz, J ax=2.3 Hz, 1H), 6.75 (d, J=2.3Hz, 1H), 5.3 (br s, 2H), 2.9 (t, J=5.6 Hz, 2H), 2.55 (t, J=5.6 Hz, 2H).

6-Aminoindan-1-one (10.0 g, 68 mmol) was treated with pyridine (50 ml) and hydroxylamine-O-benzyl ether.HCl (11.4 g, 71.3 mmol) and heated to 50° C. under $N_2$ for 40 min. The mixture was evaporated in vacuo and diluted with $CH_2Cl_2$ (300 ml). Filtration gave a solid which was washed with a small volume of $CH_2Cl_2$ and dried in vacuo to give 6-Amino-1-O-benzyloximinoindane (14.0 g, 48.5 mmol) as the HCl salt. NMR (DMSO) 10.5–9.0 (br s, 3H), 7.5–7.3 (m, 8H), 5.2 (s, 2 H), 3.05 (m, 2H), 2.9 (m, 2H).

6-Amino-1-O-benzyloximinoindane.HCl (5.0 g, 17.3 mmol) was treated with 1.0M BH3-THF (86 ml) and warmed under $N_2$ to 40° C. for 23 hrs. The mixture was evaporated and diluted with $CH_2Cl_2$ and quenched by dropwise adition of MeOH. The solvent was evaporated and 1.0N HCl (50 ml) was added and the mixture warmed to 50° C. for 1hr. After cooling, 1.0N NaOH (50 ml) was added and the pH adjusted to 9.5 with additional 1.0N NaOH. The mixture was extracted with $CH_2Cl_2$ and the extract evaporated onto silica gel and chromatographed using $CH_2Cl_2$ with 30 volume % MeOH. Evaporation of appropriate fractions gave 1,6-diaminoindane (2.0 g, 78%). NMR (DMSO-$d_6$) 6.8 (d, J=6.8 Hz, 1H), 6.57 (s, 1H), 6.4 (d, J=6.8 Hz, 1H), 4.8 (brs, 2H) 4.0 (t, J=7Hz, 1H), 2.75–2.6 (m, 2H), 2.3–2.2 (m, 1H), 1.8 (br s, 2H, $NH_2$), 1.6–1.4 (m, 1H).

1,6-Diaminoindane ( 0.5 g, 3.4 mmol) was stirred in $CH_2Cl_2$ (10 ml) and cooled to 0° C. Di-tert-butyl dicarbonate (0.74 g, 3.4 mmol) in $CH_2Cl_2$ (3 ml) was added dropwise over 10 min and the solution stirred overnight. The solution was evaporated in vacuo and diluted with EtOH (20 ml) and cooled to 0° C. Intermediate C was added and the mixture allowed to warm to 20° C. and stirred for 90 min. Dropwise addition of 30% HBr/HOAc (1.5 ml) with stirring gave after 70 min a white solid which was collected and washed with a small volume of $CH_2Cl_2$ and dried in vacuo yielding N-(3-Amino-5-indanyl)acetamidine (1.1 g, 93%) as the 2HBr salt. NMR (DMSO-$d_6$) 8.5 (brs, NH), 8.4 (brs, NH), 7.55 (s, 1H), 7.5 (s, 1H), 7.3 (d, J=7.0 Hz, 1H), 4.8 (m, 1H), 3.8 (brs, NH), 3.2–3.0 (m, 1H), 3.0–2.8 (m, 1H), 2.6–2.5 (m, 1H), 2.4 (s, 3H, $CH_3$), 2.1–2.0 (m, 1H).

EXAMPLE 60

Preparation of N-(1-Amino-4-indanyl)acetamidine

4-Nitroindan-1-one was converted to the 1-oximinobenzylether and reduced to 1-amino-4-nitroindane using BH3-THF by the methods described in example 59.

1-Amino-4-nitroindane (0.4 g, 2.24 mmol) was dissolved in $CH_2Cl_2$ (10 ml) and treated with t-BOC anhydride (0.59 g, 2.7 mmol). After 18 hrs the solvent was removed in vacuo and the residue dissolved in EtOH (50 ml) and reduced using 5% Pd/C (0.2 g) and $H_2$ at 32 psi on a Parr apparatus. Evaporation of the solvent to a final volume of 20 ml followed Filtration on celite. The intermediate was treated with intermediate C (0.68 g, 2.3 mmol) and stirred for 2 hrs. The solvent was removed in vacuo and the residue dissolved in dioxane (15 ml) and treated with 30% HBr-HOAc. After 90 min the crystaline solid that resulted was collected and washed with a small volume of $CH_2Cl_2$ and dried in vacuo to give N-(1-Amino-4-indanyl)acetamidine (0.60 g, 99%) as the HBr salt. NMR ($D_2O$) 7.6 (d, J=7 Hz, 1H), 7.5 (dd, J=7 Hz, 1H), 7.3 (d, J=7 Hz, 1H), 4.9 (m, 1H), 3.1–2.8 (m, 2H), 2.6 (m, 1H), 2.4 (s, 3H, $CH_3$), 2.1 (m, 1H).

EXAMPLE 61

Preparation of N-6-(Aminomethyl)-1-indanyl) acetamidine

6-Cyanoindan-1-one (prepared using the procedure of Allinger and Jones, JOC 1962, p70. vol 27 for the tetralone analogue) (3.86 g, 24.5 mmol) was converted to the 1-oxime-O-benzyl ether and reduced with $BH_3$-THF by the methods described in example 59 to give 1-amino-6-(aminomethyl)indane. The diamine was isolated in 31% yield as the 2 HCl salt by treatment of an ether solution with 4.0N HCl in dioxane. 1-Amino-6-aminomethylindane 2HCl (0.5 g, 2.1 mmol) was stirred in EtOH (20 ml), cooled to 0° C. and treated with $NEt_3$ (0.59 ml, 4.2 mmol). Intermediate A (0.43 g, 2.1 mmol) was added and the mixture was allowed to warm to 20° C. and stir overnight. The white crystaline product was collected and washed with a small volume of ether and dried in vacuo to give N-(6-(Aminomethyl)-1-indanyl)acetamidine (0.27 g, 35%) as the 2 HCl salt NMR ($D_2O$) 7.45–7.25 (m, 3H), 4.8 (m, 1H), 4.45 (s, 2H), 3.2–2.85 (m, 2H), 2.6)m, 1H), 2.2 (s, 3H, $CH_3$), 2.1 (m, 1H).

EXAMPLE 62

Preparation of N-((3-Amino-5-indanyl)methyl) acetamidine

1-Amino-6-aminomethylindane . 2 HCl (2.0 g, 8.5 mmol) was stirred in MeOH and cooled to 0° C. and treated with $Et_3N$ (1.8 ml, 12.9 mmol). Di-tert-Butyl dicarbonate (1.0 g, 4.6 mmol) in $CH_2Cl_2$ (3 ml) was added dropwise over 10 min and the mixture allowed to warm to 20° C. and stirred for 60 min. The mixture was evaporated in vacuo followed by treatment with $CH_2Cl_2$ (15 ml) gave a white solid which was collected and dried in vacuo to yield 1-amino-6-tert-butylcarbamoylmethylindane HCl (0.46 g, 18%). NMR (DMSO) 8.3 (br s, $NH_3$), 7.4 (br s, 2H, NHCO), 7.25 (d, J=7.6 Hz, 1H), 7.2 (d, J=7.6 Hz), 4.7 (t, J=6 Hz, 1H), 4.13 (d, J=6 Hz, 2H), 3.15–2.95 (m, 1H), 2.95–2.75 (m, 1H), 2.5–2.4 (m, 1H), 2.1–1.9 (m, 1H), 1.4 (s, 9H).

1-Amino-6-tert-butylcarbamoylmethylindane hydrochloride (0.15 g, 0.57 mmol) was stirred in EtOH (3 ml) at 0° C. and treated with $Et_3N$ (0.08 ml, 0.57 mmol). Intermediate A (0.115 g, 0.57 mmol) was added and the mixture allowed to warm to 20° C. and stir overnight. The mixture was evaporated in vacuo and the residue dissolved in dioxane (3 ml) and treated dropwise with 4.0N HCl/dioxane (1.0 ml). On standing at 5° C. overnight, a white crystaline solid formed and was collected and washed with a small volume of cold dioxane and dried in vacuo to give N-(3-Amino-5-indanyl) methyl)acetamidine (0.10 g, 63%) as the 2 HCl salt. NMR ($D_2O$) 7.4–7.3 (m, 3H), 5.2 (m, 1H), 4.1 (s, 2H), 3.1–2.8 (m, 2H), 2.6 (m, 1H), 2.2 (s, 3H, $CH_3$), 2.0 (m, 1H).1H), 3.0–2.8 (m, 1H), 2.6–2.5 (m, 1H), 2.4 (s, 3H, $CH_3$), 2.1–2.0 (m, 1H).

EXAMPLE 63

Preparation of 1-Amino-4-(1-iminoethylamino)but-2-yne 2.5hydrochloride

Preparation of 1-Azido-4-(butoxycarbonylamino)but-2-yne

Hexamethylenetetramine (28.27 g) and 1,4-dichlorobut-2-yne (24.84 g) were refluxed in chloroform (165 ml) for 20 min. Upon cooling to room temperature the resulting precipitate was filtered off and sucked dry. The mother liquor was concentrated to one quarter volume and a further crop of precipitate obtained. Total yield of complex=46.10 g.

The above complex (6.7 g) was added to a mixture of ethanol (100 ml) and concentrated hydrochloric acid (9.4 ml) and the mixture refluxed for 3 h. On cooling, the precipitate was filtered and discarded. The filtrate was concentrated until it became cloudy at which point it was diluted with diethyl ether (4 volumes). The resulting precipitate was filtered, washed with more diethyl ether and sucked dry. The filtrate was concentrated to a small volume, more diethyl ether added and the resulting precipitate filtered off and sucked dry. The total yield of 1-amino-4-chlorobut-2-yne hydrochloride was 2.924 g.

1-Amino-4-chlorobut-2-yne hydrochloride (6 g) and di-t-butyldicarbonate (9.354 g) in dry THF (60 ml) were treated with diethylisopropylamine (7.52 ml) and the mixture stirred overnight at room temperature. After this time the precipitate was filtered off and the filtrate concentrated in vacuo. The residue was partitioned between diethyl ether and water and the organic layer washed successively with 0. 1N HCl, water and brine, and dried over $MgSO_4$. Concentration in vacuo gave a green oil (9.205 g) which was used directly. The oil was dissolved in DMF (140 ml) and tetrabutylammonium iodide (7.92 g) and sodium azide (3.065 g) added. The mixture was heated under $N_2$, in the dark at 60°–70° C. for 1 h. Upon cooling, diethyl ether and water were added and the organic layer washed successively with 0.1N HCl, water and brine, and dried over $MgSO_4$. Concentration in vacuo gave an oil which was purified by column chromatography on silica gel (3/1 hexane/ethyl acetate). The fractions with Rf=0.42 (3/1 hexane/ethyl acetate) pooled and concentrated to yield 1-azido-4-(butoxycarbonylamino)but-2-yne as a yellow oil (3.049 g).

Preparation of 1-Amino-4-(iminoethylamino)but-2-yne 2.5hydrochloride

To 1-azido-4-(butoxycarbonylamino)but-2-yne (0.294 g) in dry THF (7 ml) was added triphenyl phosphine (0.386 g) and water (38 ml) and the mixture stirred overnight at room temperature. After this time S-benzyl-2-thioacetimidate hydrochloride (0.237 g) and ethanol (4 ml) were added and the mixture stirred overnight at room temperature. The mixture was concentrated in vacua, the residue partitioned between water and ethyl acetate. and the aqueous layer concentrated in vacuo. The residue was treated with ethanol and re-concentrated in vacuo (×2). The residue was tritured with diethyl ether and the ether decanted off (×2). The remaining solid was sucked dry on an oil pump to yield 1-butoxycarbonylamino-4-(1-iminoethylamino)but-2-yne hydrochloride as a white hygroscopic solid (0.332 g).

1-Butoxycarbonylamino-4-(1-iminoethylamino)but-2-yne (0.332 g) was deprotected by treatment with 4 N HCl/dioxane (3 ml) at 0° C. and stirring at 0° C. for 1h then at room temperature for 1h. After this time the mother liquor was decanted off and the sticky residue subjected to an oil pump vacuum to remove residual solvent. The resulting material was triturated with dry diethyl ether (×2), filtered off and washed with more dry diethyl ether. The yellow solid was finally dried in a drying pistol to yield 1-amino-4-(1-iminoethylamino)but-2-yne 2.5hydrochloride (0.184 g), Mpt 182°–185° C.(dec), FAB M.S. $M+1^+$126.

EXAMPLE 64

Preparation of 1-Amino-4-(1-imino-2-fluoroethylamino)but-2-yne dihydrobromide 1-Amino-4-(1-imino-2-fluoroethylamino)but-2-ynedihydrobromide was made from 1-azido-4-(butoxycarbonylamino)but-2-yne and S-benzyl-2-fluorothioacetimidate hydrobromide to yield 1-butoxycarbonylamino-4-(1-imino-2-fluoro-ethylamino) but-2-yne hydrobromide as an intermediate.

1-Butoxycarbonylamino-4-(1-imino-2-fluoroethylamino) but-2-yne hydrobromide (500 mg) was deprotected by dissolving in glacial acetic acid (10 ml), cooling until the solution almost solidified and adding HBr in acetic acid (45% wv, 1.8 ml). The mixture was stirred with cooling for 1 h then at room temperature for 1 h. After this time the mother liquor was decanted off and the sticky residue subjected to an oil pump vacuum to remove residual solvent. The resulting material was triturated with dry diethyl ether (×2), filtered off and washed with more dry diethyl ether. The yellow solid was recrystallised from ethanol/diethyl ether and finally dried in a drying pistol to yield 1-amino-4-(1-imino-2-fluoroethylamino)but-2-yne dihydrobromide, Mpt 174°–176.5° C.(dec.), FAB M.S. $M+1^+$144.

EXAMPLE 65

Preparationof1-(2-Aminoethoxy)-2-N-(1-iminoethyl) ethylamine2hydrochloride

Preaparation of N-(tertbutoxycarbonyl)-2-(2-aminoethoxy) ethyl azide

The title compound was prepared from 2-(2-aminoethoxy)ethanol using the procedures described for equivalent non-ether linked straight chain aminoalcohols by Mattingly (Synthesis, 1990, 366–368).

Preparation of 1-(2-Aminoethoxy)-2-N-(1-iminoethyl) ethylamine 2hydrochloride

To N-(tertbutoxycarbonyl)-2-(2-aminoethoxy)ethyl azide (0.315 g) in dry THF (10 ml) was added polymer supported triphenyl phosphine (0.46 g) and water (37 μl) and the mixture slowly stirred overnight at room temperature. After this time S-benzyl-2-thioacetimidate hydrochloride (0.352 g) and ethanol (5 ml) were added and the mixture stirred overnight at room temperature. The mixture was concentrated in vacuo, the residue partitioned between water and ether, and the aqueous layer concentrated in vacuo to furnish N-(tertbutoxycarbonyl)-1-(2-Aminoethoxy)-2-N-(1-iminoethyl) ethylamine as a white foam.

Treatment of a solution of N-(tertbutoxycarbonyl)-1-(2-Aminoethoxy)-2-N-( 1-iminoethyl) ethylamine (280 mg) in dioxan with 10 ml of 4N HCl in dioxan served to deprotect the molecule by stirring at room temperature for 1 h. At this time a 50 ml portion of ether and the suspension were vigorously stirred. The title compound was furnished as a hygroscopic solid on filtering this suspension and drying in vacuo.

FAB MS M+1$^+$, 100%. 1H NMR (360 MHz, $D_2O$) $\delta_H$, ppm 2.28 (1H, s, Me); 3.25 (2H, t, $CH_2$), 3.55 (2H, t $CH_2$), 3.82 (4H, m, 2× $CH_2$), IR $\nu_{max}$ (KBr disc) 3 111, 1 676, 1 643 cm$^{-1}$

Biological Data

NO synthase inhibition was determined by the following procedure:

Purification of NOS from human placenta

Amion and chorion were removed from fresh placenta, which was then rinsed with 0.9% NaCl. The tissue was homogenised in a Waring blender in 3 volumes of HEDS buffer (20 mM Hepes pH 7.8, 0.1 mM EDTA, 5mM DTT, 0.2M sucrose) plus 0.1 mM PMSF. The homogenate was filtered through cheesecloth and then centrifuged at 1000 g for 20 min. The supernatant was recentrifuged at 27,500 g for 30 min. Solid ammonium sulphate was added to the supernatant to give 32% saturation. Precipitated protein was pelleted at 25,000 g and then redissolved in a minimal volume of HEDS buffer plus 0.1 mM PMSF, 10 μg/ml leupeptin and soybean trypsin inhibitor, and 1 μg/ml pepstatin. The redissolved pellet was centrifuged at 15,000 g for 10 min. To the supernatant was added 1/20 volume at 2,5' ADP agarose resin (Sigma), and the slurry was mixed slowly overnight. In the morning, slurry was packed into a column. The resin was sequentially washed with HEDS, 0.5M NaCl in HEDS, HEDS, and then NOS was eluted with 10 mM NADPH in HEDS. The enzyme could be concentrated by ultra filtration and quick frozen and stored at −70° C. without loss in activity for at least 3 months.

Assay for human placental NOS

NOS was assayed for the formation of citrulline following the procedure of Schmidt et al (PNAS 88 365–369, 1991) with these modifications: 20 mM Hepes, pH 7.4, 10 μg/ml calmodulin, 2.5 mM CaC12, 2.5 mM DTT, 125 μM NADPH, 10 μM tetrahydrobiopterin, 0.5 mg/ml BSA, and 1 μM L-[$^{14}$C]arginine (New England Nuclear). Linearity of NOS-catalysed rate was confirmed prior to kinetic studies that used single time point determination of rate.

Purification of NOS from cytokine-induced human colorectal adenocarcinoma DLD-1 cells DLD-1 (ATCC No. CCL 221) were grown at 37° C., 5% $CO_2$ in RPMI 1640 medium supplemented with L-glutamine, penicillin, streptomycin, and 10% heat-inactivated fetal bovine serum. Cells were grown to confluence and then the following cocktail of cytokines were added: 100 units/ml interferon-gamma, 200 units/ml interleukin-6, 10 ng/ml tumour necrosis factor, and 0.5 ng/ml interleukin-1β At 18–24 hr post-induction, cells were harvested by scraping and washed with phosphate-buffered saline. Pelleted cells were stored at −70° C. Purification of the induced NOS was performed at 4° C. Crude extract was prepared by three cycles of freeze/thawing cells in TDGB (20 mM tris pH 7.5, 10% glycerol, 1 mM DTT, 2 μM tetrahydrobiopterin). Extract was applied directly onto a column of 2', 5' ADP sepharose (Pharmacia). Resin was sequentially washed with TDGB, 0.5M NaCl in TDGB, TDGB. NOS was eluted with 2 mM NADPH in TDGB. BSA was immediately added to give a final concentration of 1 mg/ml. NOS could be quick frozen and stored at −70° C. without loss in activity for at least 2 months.

Assay for inducible human NOS

The formation of citrulline were assayed as described above except that 10 μM FAD was included and calmodulin and $CaCl_2$ excluded from the assay mix.

Purification of NOS from human brain

Human brain NOS was prepared using variations of the procedures of Schmidt et al. (PNAS 88 365–369, 1991), Mayer et al. (Fed. Eur. Biochem. Soc. 288 187–191, 1991), and Bredt and Snyder, (PNAS 87 682–685, 1990). Briefly, fresh whole brains (3 with myelinated tissue dissected away, 1050 g) were homogenised in cold buffer A (50 mM HEPES, pH 7.5 (pH at RT) and 0.5 mM EDTA, 10 mM DTT, 3.6 L total volume) with a polytron. The mixture was centrifuged at 13,000 g for 1 hour and the supernatant fluid was removed (about 2050 ml). To the supernatant fluid, solid ammonium sulphate (365 g, about 30% of saturation) was added and stirred slowly for a total of 30 minutes. The precipitate was pelleted at 13,000 g for 30 minutes and the pellet was resuspended in ~400 ml of buffer A with 4 μM tetrahydrobiopterin, 1 μM FAD (Sigma), and 1 μM FMN (Sigma). The solution was centrifuged at 41,000 g for 60 minutes. The supernatant was removed, frozen by pouring into liquid nitrogen, and stored overnight at −70° C. The mixture was thawed and passed through at 2', 5' ADP-agarose column (0.4 g swelled in buffer A) at 4 ml/min. The column was washed with 100 ml buffer A, 200 ml buffer A with 500 mM NaCl, 100 ml Buffer A, then 30 ml buffer A with 5 mM NADPH. To the enzyme solution was added tetrahydrobiopterin to 10 μM, FAD and FMN to 1 μM, and Tween to 0.1%. This solution was concentrated by Centriprep-30 to a volume of approximately 500 μl. Enzyme activity was determined as described by Schmidt et al. 1991, except that 10 μM tetrahydrobiopterin was included in the assay.

The compounds of the invention exhibit NOS inhibition properties, and certain groups of the compounds exhibit selective inhibition properties against either the inducible or neuronal NOS.

We claim:

1. [An] *A method of treating a condition requiring inhibition of NO synthase, the step of administering to a mammal in need thereof an effective amount of an* acetamidine derivative of formula (I):

(I)

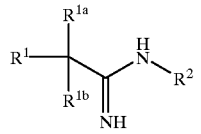

or a salt thereof, wherein $R^1$ is hydrogen, a $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl; provided that $R^3$ is not $NR^5R^6$ when X is oxygen or $S(O)_n$;

$R^{1a}$ and $R^{1b}$ are independently selected from hydrogen and halo;

$R^2$ is a group:

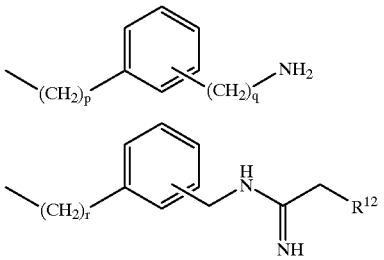

wherein p, q and r are independently 0, 1 or 2, and $R^{12}$ is selected from the group consisting of flouro, hydrogen, and $NH_2$.

2. A *method of treating a condition requiring inhibition of NO synthase, comprising the step of administering to a mammal in need thereof an effective amount of a* compound of formula (1B):

(1B)

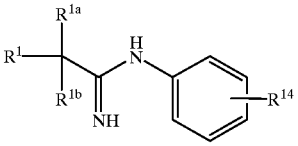

wherein $R^1$ is hydrogen, a $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl, provided that $R^3$ is not $NR^5R^6$ when X is oxygen or $S(O)_n$;

$R^{1a}$ and $R^{1b}$ are independently selected from hydrogen and halo, and $R^{14}$ represents one or two substituents on the phenyl ring independently selected from halo, $ZR^7$ or a group:

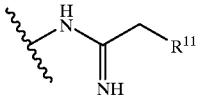

wherein Z is oxygen, $C(O)_m$ wherein m is 1 or 2, $S(O)_n$ wherein n is 0, 1 or 2, or a group $NR^8$ wherein $R^8$ is hydrogen or $C_{1-6}$ alkyl, $R^7$ is hydrogen, $C_{1-6}$ alkyl, or a group $NR^9R^{10}$ wherein $R^9$ and $R^{10}$ are independently hydrogen or $C_{1-6}$ alkyl, and $R^{11}$ has a definition the same as for $R^1$, or $R^{14}$ is a [$C_{1-6}$] $C_{1-8}$ hydrocarbyl group optionally substituted by one or two groups which may be the same or different, and are selected from halo, $ZR^7$ or a group:

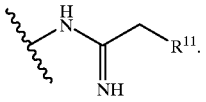

3. *A method of treating a condition requiring inhibition of NO synthase, comprising the step of administering to a mammal in need thereof an effective amount of a* compound of formula 1C:

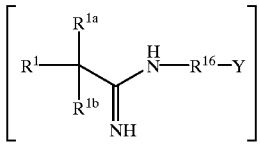

(1C)

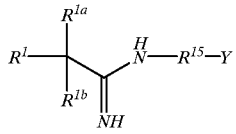

wherein $R^1$ is hydrogen, a $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl, provided that $R^3$ is not $NR^5R^6$ when X is oxygen or $S(O)_n$;

$R^{1a}$ and $R^{1b}$ are independently selected from hydrogen and halo;

$R^{15}$ is a bond or $CH_2$; and

Y is selected from the group consisting of optionally substituted phenyl and indanyl; wherein Y is optionally substituted by one or more groups independently selected from the group consisting of halo, amino, cyano, nitro, hydroxy, and $C_{1-6}$ hydrocarbyl optionally substituted by hydroxy, $C_{1-6}$ alkoxy, $C_{1-6}$ thioalkyl, $CF_3$, [$N^3$] $N_3$, a group:

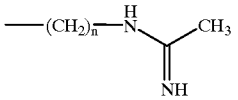

wherein n is 0, 1 or 2, $C(O)_mB'$ or $S(O)_nB'$ wherein m is 1 or 2, n is 0, 1 or 2 and B' is amino or $C_{1-6}$ alkyl, a group:

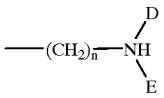

wherein n is 0, 1 or 2 and D and E are independently selected from the group consisting of hydrogen, hydroxy, amino, $C_{1-6}$ alkyl, —$CNHCH_3$, —$CO_2{}^tBu$, a group:

[—$(CH_2)_n$—NH—$(CH_2)_n$—A]

*—$(CH_2)_n$—NH—$(CH_2)_n$—A* wherein n is 0, 1 or 2, n' is 0, 1 or 2, and A is phenyl

*a group:*

*—$(CH_2)_n$—G*

*wherein n is 0, 1 or 2 and G is —$CO_2H$, or —$CO_2C_{1-6}$ alkyl.*

4. [The] *An* acetamidine derivative [of claim 1] which is:

N-(3-(Hydroxymethyl)phenyl)acetamidine;

N-(3-(Aminomethyl)phenyl)acetamidine;

N-(3-((Methylamino)methyl)phenyl)acetamidine;

N-(Dimethylamino)methyl)phenyl)acetamidine;

N-(3-(Aminomethyl)phenyl)-2-fluoroacetamidine;

N-(3-(2-Aminoethyl)phenyl)acetamidine*; or*

*a salt thereof.*

5. [The] *An* acetamidine derivative [of claim 1] which is:

N-(3-(Aminomethyl)benzyl)acetamidine;

N-(4-(Aminomethyl)benzyl)acetamidine;

N-(3-(Aminomethyl)benzyl)-3-fluoroacetamidine;

N-(3-(Aminomethyl)benzyl-2-aminoacetamidine;

N-(3-(Aminomethyl)benzyl)-2,2,2-trifluororacetamidine;

N-((1H-Indazol-6-yl)methyl)acetamidine; [or]

N-((3-Amino-5-indanyl)methyl)acetamidine*; or*

*a salt thereof.*

6. The acetamidine derivative of claim [1] *5* which is:

N-(3-(Aminomethyl)benzyl)acetamidine;

N-(4-(Aminomethyl)benzyl)acetamidine;

N-(3-(Aminomethyl)benzyl)-3-fluoroacetamidine;

N-(3-(Aminomethyl)benzyl)-3-aminoacetamidine;

N-((3-Amino-5-indanyl)methyl)acetamidine;

or a salt thereof.

7. A pharmaceutical formulation comprising at least one compound [as defined in claim 1] *of formula (I):*

(I)

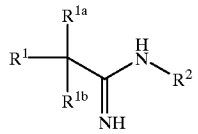

*or a salt thereof, wherein*

*$R^1$ is*

*hydrogen,*

*a $C_{1-6}$ hydrocarbyl group substituted by halo,*

*halo,*

*nitro,*

*cyano or*

*a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl; provided that $R^3$ is not $NR^5R^6$ when X is oxygen or $S(O)_n$;*

*$R^{1a}$ and $R^{1b}$ are independently selected from hydrogen and halo;*

*$R^2$ is a group:*

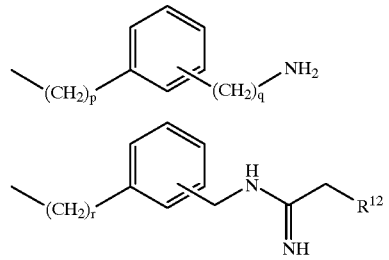

*wherein p, q and r are independently 0, 1 or 2, and $R^{12}$ is selected from the group consisting of flouro, hydrogen, and $NH_2$;* together with one or more pharmaceutically acceptable carriers, diluents, or excipients. [

8. A method of treating a condition requiring inhibition of NO synthase, comprising the step of administering to a mammal in need thereof an effective amount of an acetamidine derivative of claim 1.]

9. The method of claim [8] *1* wherein the compound inhibits one of the NO synthase isoenzymes with little or no inhibition of the other isoenzymes.

10. A method for the prophylaxis or treatment of shock states resulting from overproduction of NO by iNOS, said method comprising administering an acetamidine derivative of [claim 1] *formula (I):*

(I)

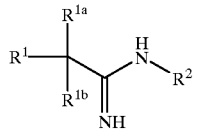

*or a salt thereof, wherein*

$R^1$ is hydrogen, a $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl; provided that $R^3$ is not $NR^5R^6$ when X is oxygen or $S(O)_n$;

$R^{1a}$ and $R^{1b}$ are independently selected from hydrogen and halo;

$R^2$ is a group:

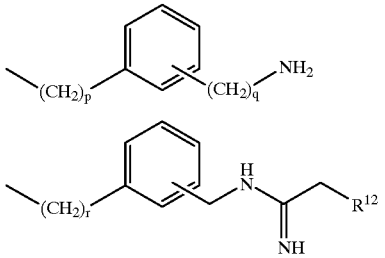

wherein p, q and r are independently 0, 1 or 2, and $R^{12}$ is selected from the group consisting of flouro, hydrogen, and $NH_2$;

in an amount effective to prevent or treat shock states resulting from overproduction of NO by iNOS.

11. The method of claim 10 wherein the condition is selected from the group consisting of septic shock, shock caused by fulminant heptic failure, shock caused by therapy with one or more cytokines and shock caused by therapy with cytokine-inducing agents.

12. A method of treating a condition requiring inhibition of NO synthase, which comprises the step of administering to a mammal a pharmaceutical formulation according to claim 7 in an amount effective to inhibit NO synthase.

13. A method for the prophylaxis or treatment of an auto-immune disease or an inflammatory disease, said method comprising administering an acetamidine derivative of [claim 1] formula (1):**

(I)

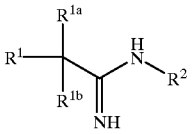

or a salt thereof, wherein $R^1$ is hydrogen, a $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl; provided that $R^3$ is not $NR^5R^6$ when X is oxygen or $S(O)_n$;

$R^{1a}$ and $R^{1b}$ are independently selected from hydrogen and halo;

$R^2$ is a group:

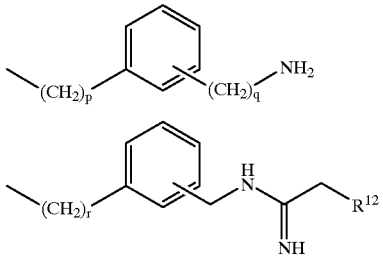

wherein p, q and r are independently 0, 1 or 2, and $R^{12}$ is selected from the group consisting of flouro, hydrogen, and $NH_2$;

in an amount effective to prevent or treat an auto-immune disease or an inflammatory disease.

14. A method for the prophylaxis or treatment of a condition resulting from the overproduction of NO by nNOS, said method comprising administering an acetamidine derivative of [claim 1] formula (I):**

(I)

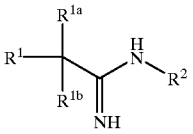

or a salt thereof, wherein $R^1$ is hydrogen, a $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl; provided that $R^3$ is not $NR^5R^6$ when X is oxygen or $S(O)_n$;

$R^{1a}$ and $R^{1b}$ are independently selected from hydrogen and halo;

$R^2$ is a group:

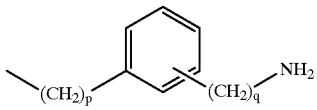

-continued

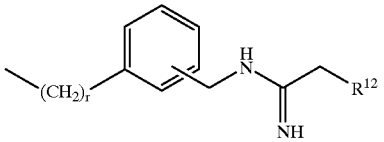

*wherein p, q and r are independently 0, 1 or 2, and $R^{12}$ is selected from the group consisting of flouro, hydrogen, and $NH_2$;* in an amount effective to prevent or treat conditions resulting from the overproduction of NO by nNOS.

15. A process for the preparation of [a compound of formula (1)

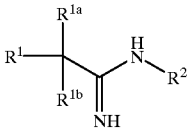

or a salt thereof, wherein $R^1$ is hydrogen, a $C_{1-6}$ hydrocarbyl group optionally substituted by halo, halo, nitro, cyano or a group $XR^3$ wherein X is oxygen, $C(O)_m$ wherein m is 1 or 2, $S(O)_n$ wherein n is 0, 1 or 2, or a group $NR^4$ wherein $R^4$ is hydrogen or $C_{1-6}$ alkyl; and $R^3$ is hydrogen, $C_{1-6}$ alkyl, or a group $NR^5R^6$ wherein $R^5$ and $R^6$ are independently hydrogen or $C_{1-6}$ alkyl, provided that $R^3$ is not $NR^5R^6$ when X is oxygen or $S(O)_n$;

$R^{1a}$ and $R^{1b}$ are independently selected from hydrogen and halo;

$R^2$ is a $C_{1-14}$ hydrocarbyl group the group $R^2$ being optionally substituted by one or more groups independently selected from halo; $N_3$; nitro; $CF_3$; $ZR^7$ wherein Z is oxygen, $C(O)_m$ wherein m is 1 or 2, $S(O)_n$ wherein n is 0, 1 or 2, or a group $NR^8$ wherein $R^8$ is hydrogen or $C_{1-6}$ alkyl and $R^7$ is hydrogen, $C_{1-6}$ alkyl or a group $NR^9R^{10}$ wherein $R^9$ and $R^{10}$ are independently hydrogen or $C_{1-6}$ alkyl; or $R^2$ is substituted by a group

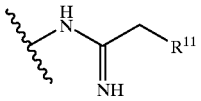

wherein $R^{11}$ has a definition the same as $R^1$;

with the proviso that when $R^1$ is a $C_{1-6}$ alkyl group and $R^2$ is a $C_{1-14}$ hydrocarbyl substituted by two groups $ZR^7$ wherein one group $ZR^7$ is $CO_2H$, the other group $ZR^7$ is not $NH_2$;] *N-(3-(aminomethyl)benzyl)acetamidine* said process comprising the reaction of [an amine of formula (II):

$H_2N—R^2$]

*tert-butyl N-(3-aminomethyl)benzyl* or a protected derivative thereof;

with *benzylthioacetamidate hydrochloride*

[a 1-benzylthioethaniminium derivative of formula (III)

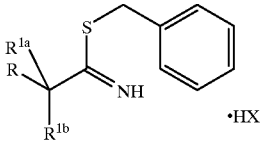

(III)]

followed by deprotection if necessary.

*16. The acetamidine derivative of claim 5 which is N-(3-(aminomethyl)benzyl)acetamidine or a salt thereof.*

* * * * *